United States Patent [19]

Okumura et al.

[11] Patent Number: 5,629,321

[45] Date of Patent: May 13, 1997

[54] BICYCLIC COMPOUND AND PLATELET AGGREGATION INHIBITOR CONTAINING THE SAME

[75] Inventors: Kunio Okumura, Chiba-ken; Isao Yokoyama, Osaka-fu; Toshiyuki Shimazaki, Chiba-ken; Michihiko Miyamoto, Fukuoka-ken; Hiroyuki Yamashita, Chiba-ken; Kenji Kibayashi, Chiba-ken; Takanori Yutaka, Chiba-ken; Kouhei Yazawa, Chiba-ken, all of Japan

[73] Assignee: Mitsui Toatsu Chemicals, Inc., Tokyo, Japan

[21] Appl. No.: 544,583

[22] Filed: Oct. 18, 1995

[30] Foreign Application Priority Data

Oct. 27, 1994 [JP] Japan ................................. 6-264188

[51] Int. Cl.⁶ ........................... A61K 31/19; A61K 31/35; A61K 31/47; C07D 217/16; C07D 309/22; C07C 63/36

[52] U.S. Cl. ...................... 514/307; 514/456; 514/561; 514/564; 514/563; 546/147; 549/398; 562/490; 558/11

[58] Field of Search ................... 546/147; 514/307, 514/456, 561, 564; 549/398; 562/490; 558/11

[56] References Cited

FOREIGN PATENT DOCUMENTS

W0A9429273 12/1994 WIPO.

OTHER PUBLICATIONS

Cook et al, Platelet Glycoprotein IIb/IIIa Antagonists, *Drugs of the Future*, vol. 19, No. 2, pp. 135–159, 1994.

Primary Examiner—David B. Springer
Attorney, Agent, or Firm—Burns, Doane, Swecker & Mathis

[57] ABSTRACT

The invention relates to a novel compound which is represented by the formula (1) and has an excellent platelet aggregation inhibiting action based on fibrinogen antagonism. The platelet aggregation inhibitor containing the compound of the formula (1) as an effective ingredient are effective for prevention and curing of thrombosis and restenosis or reocclusion after percutaneous transluminal coronary angioplasty or percutaneous transluminal coronary recanalization.

27 Claims, No Drawings

BICYCLIC COMPOUND AND PLATELET AGGREGATION INHIBITOR CONTAINING THE SAME

BACKGROUND OF THE INVENTION

1. Field of the Invention

The present invention relates to a novel bicyclic compound and a platelet aggregation inhibitor containing the same or a derivative of the same.

The platelet aggregation inhibitor of the invention is useful as a preventive or a remedy of thrombosis such as an ischemic cardiac disease, ischemic brain disease, peripheral circulatory impairment, arterial thrombus, arterial sclerosis and pulmonary vascular impairment, and also as a preventive or a remedy of restenosis or reocclusion after percutaneous transluminal coronary angioplasty or percutaneous transluminal coronary recanalization.

2. Description of Related Art

Various medicines for inhibiting aggregation of platelets have been used for the curing of thrombosis since the platelets were found to play an important role for a crysis of the thrombosis. The aggregation of platelets is induced by various stimuli such as ADP, collagen, epinephrine, thrombin, thromboxane A, and platelet activating factors. Therefore, anti-platelet drugs exhibit an inhibiting effect merely for the platelet aggregation caused by restricted kinds of stimulus and thus validity of these drugs is limited. On the other hand, the final step in the platelet aggregation process is a mutual combination of platelets by way of fibrinogen. The step is common and independent of the kind of aggregation eliciting stimulus. Consequently, in recent years, focused on an anti-platelet drug which directly inhibits the combination of platelets and fibrinogen. Such a drug inhibits the whole aggregation eliciting stimuli. It has been found that the binding site of fibrinogen for platelets is glycoprotein GP II b/III m a which is present in a platelet membrane and that the structure of -Arg-Gly-Asp- in a fibrinogen molecule has a minimum amino acid sequence which is required for combination with GP II b/III a. Many non-peptide compounds which are similar in structure to the straight chain or cyclic peptide compound having the amino acid sequence of -Arg-Gly-Asp- have been reported thereafter [Drug of the Future, 19(2), 135(1994) and 19(5), 461(1994)]. The common structure of the so far known non-peptide compounds has an acid group such as a carboxyl group which corresponds to a carboxyl group in aspartic acid and in a certain distance a basic group such as an amidino group, guanidino group, piperadinyl group and aminomethyl group which correspond to a guanidino group in arginine. Further, diversity has been found on the skeleton structure which connects the acid group with the basic group. WO 94/29273 has disclosed bicyclic compounds formed by condensation of two six-membered rings as the skeleton structure. However, WO 94/29273 has practically described only three compounds which have a tetrahydroisoquinoline structure. The inhibiting action of these compounds for human platelet aggregation is 1–13 μM at $IC_{50}$, and thus the activity is still unsatisfactory for an anti-platelet drug.

SUMMARY OF THE INVENTION

As a result of an intensive investigation on a non-peptide compound having fibrinogen antagonism, the present inventors have found a novel bicyclic compound having an extremely strong action for inhibiting platelet aggregation. Thus the present invention has been completed.

That is, the aspect of the invention is a novel compound represented by the formula (1) or a pharmaceutically acceptable salt of the same.

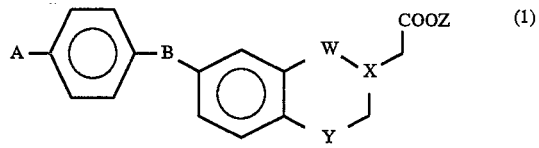

wherein A is an amidino, guanidino or aminomethyl group, B is $-CH_2O-$, $-OCH_2-$, $-CH_2N(R^1)-$, $-N(R^1)CH_2-$, $-CON(R^1)-$ or $-N(R^1)CO-$, wherein $R^1$ is a hydrogen atom or an alkyl group having 1–4 carbon atoms; W-X is

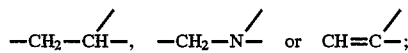

Y is $-CH_2-$ or $-O-$; and Z is a hydrogen atom or an alkyl group having 1–4 carbon atoms.

Another aspect of the invention is a platelet aggregation inhibitor comprising the compound represented by the formula (1) as an active ingredient.

A further aspect of the invention is a preventive or a remedy for thrombosis and restenosis or reocclusion after percutaneous transluminal coronary angioplasty or endermic percutaneous transluminal coronary recanalization, comprising a compound represented by the formula (1) as an active ingredient.

Still another aspect which is included in the invention is a compound represented by the formula (2) or a pharmaceutically acceptable salt of the same.

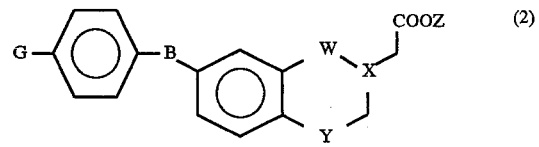

wherein G is a cyano group or $HN=C(OR^2)-$, wherein $R^2$ is an alkyl group having 1–4 carbon atoms; B is $-CH_2O-$, $-OCH_2-$, $-CH_2N(R^1)-$, $-N(R^1)CH_2-$, $-CON(R^1)-$ or $-N(R^1)CO-$, wherein $R^1$ is a hydrogen atom or an alkyl group having 1–4 carbon atoms; W-X is

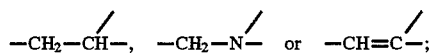

Y is $-CH_2-$ or $-O-$; and Z is a hydrogen atom or an alkyl group having 1–4 carbon atoms.

The compound represented by the formula (2) is very useful as an intermediate of synthesis for the compound of the formula (1) wherein A is an amidino group.

DETAILED DESCRIPTION OF THE INVENTION

The present invention will hereinafter be illustrated in detail.

In the invention, the alkyl group having 1–4 carbon atoms is a methyl, ethyl, n-propyl, isopropyl, n-butyl, isobutyl, sec-butyl, or tert-butyl.

Representative compounds of the formula (1) in the invention will be practically exemplified hereinafter as the compound numbers 1–132. However, the scope of the invention is not limited by these compounds. The compound number will be referred to in the below described examples, pharmacological test examples and pharmacutical formulation examples.

(1) 7-[(4-amidinobenzoyl)amino]-1,2,3,4-tetrahydronaphthalene-2-acetic acid
(2) methyl 7-[(4-amidinobenzoyl)amino]-1,2,3,4-tetrahydronaphthalene-2-acetate
(3) ethyl 7-[(4-amidinobenzoyl)amino]-1,2,3,4-tetrahydronaphthalene-2-acetate
(4) n-propyl 7-[(4-amidinobenzoyl)amino]-1,2,3,4-tetrahydronaphthalene-2-acetate
(5) isopropyl 7-[(4-amidinobenzoyl)amino]-1,2,3,4-tetrahydronaphthalene-2-acetate
(6) n-butyl 7-[(4-amidinobenzoyl)amino]-1,2,3,4-tetrahydronaphthalene-2-acetate
(7) sec-butyl 7-[(4-amidinobenzoyl)amino]-1,2,3,4-tetrahydronaphthalene-2-acetate
(8) tert-butyl 7-[(4-amidinobenzoyl)amino]-1,2,3,4-tetrahydronaphthalene-2-acetate
(9) 7-[N-(4-amidinophenyl)carbamoyl]-1,2,3,4-tetrahydronaphthalene-2-acetate acid
(10) methyl 7-[N-(4-amidinophenyl)carbamoyl]-1,2,3,4-tetrahydronaphthalene-2-acetate
(11) ethyl 7-[N-(4-amidinophenyl)carbamoyl]-1,2,3,4-tetrahydronaphthalene-2-acetate
(12) n-propyl 7-[N-(4-amidinophenyl)carbamoyl]-1,2,3,4-tetrahydronaphthalene-2-acetate
(13) isopropyl 7-[N-(4-amidinophenyl)carbamoyl]-1,2,3,4-tetrahydronaphthalene-2-acetate
(14) n-butyl 7-[N-(4-amidinophenyl)carbamoyl]-1,2,3,4-tetrahydronaphthalene-2-acetate
(15) sec-butyl 7-[N-(4-amidinophenyl)carbamoyl]-1,2,3,4-tetrahydronaphthalene-2-acetate
(16) tert-butyl 7-[N-(4-amidinophenyl)carbamoyl]-1,2,3,4-tetrahydronaphthalene-2-acetate
(17) 6-[(4-amidinobenzoyl)amino]chroman-3-acetic acid
(18) methyl 6-[(4-amidinobenzoyl)amino]chroman-3-acetate
(19) ethyl 6-[(4-amidinobenzoyl)amino]chroman-3-acetate
(20) n-propyl 6-[(4-amidinobenzoyl)amino]chroman-3-acetate
(21) n-butyl 6-[(4-amidinobenzoyl)amino]chroman-3-acetate
(22) sec-butyl 6-[(4-amidinobenzoyl)amino]chroman-3-acetate
(23) tert-butyl 6-[(4-amidinobenzoyl)amino]chroman-3-acetate
(24) 6-[N-(4-amidinophenyl)carbamoyl]chroman-3-acetic acid
(25) methyl 6-[N-(4-amidinophenyl)carbamoyl]chroman-3-acetate
(26) ethyl 6-[N-(4-amidinophenyl)carbamoyl]chroman-3-acetate
(27) tert-butyl 6-[N-(4-amidinophenyl)carbamoyl]chroman-3-acetate
(28) 7-[(4-amidinobenzoyl)amino]-1,2,3,4-tetrahydroisoquinoline-2-acetic acid
(29) methyl 7-[(4-amidinobenzoyl)amino]-1,2,3,4-tetrahydroisoquinoline-2-acetate
(30) ethyl 7-[(4-amidinobenzoyl)amino]-1,2,3,4-tetrahydroisoquinoline-2-acetate
(31) n-propyl 7-[(4-amidinobenzoyl)amino]-1,2,3,4-tetrahydroisoquinoline-2-acetate
(32) isopropyl 7-[(4-amidinobenzoyl)amino]-1,2,3,4-tetrahydroisoquinoline-2-acetate
(33) n-butyl 7-[(4-amidinobenzoyl)amino]-1,2,3,4-tetrahydroisoquinoline-2-acetate
(34) sec-butyl 7-[(4-amidinobenzoyl)amino]-1,2,3,4-tetrahydroisoquinoline-2-acetate
(35) tert-butyl 7-[(4-amidinobenzoyl)amino]-1,2,3,4-tetrahydroisoquinoline-2-acetate
(36) 7-[N-(4-amidinophenyl)carbamoyl]-1,2,3,4-tetrahydroisoquinoline-2-acetic acid
(37) ethyl 7-[N-(4-amidinophenyl)carbamoyl]-1,2,3,4-tetrahydroisoquinoline-2-acetate
(38) n-propyl 7-[N-(4-amidinophenyl)carbamoyl]-1,2,3,4-tetrahydroisoquinoline-2-acetate
(39) n-butyl 7-[N-(4-amidinophenyl)carbamoyl]-1,2,3,4-tetrahydroisoquinoline-2-acetate
(40) tert-butyl 7-[N-(4-amidinophenyl)carbamoyl]-1,2,3,4-tetrahydroisoquinoline-2-acetate
(41) 7-[(4-amidinobenzoyl)amino]-3,4-dihydronaphthalene-2-acetic acid
(42) methyl 7-[(4-amidinobenzoyl)amino]-3,4-dihydronaphthalene-2-acetate
(43) ethyl 7-[(4-amidinobenzoyl)amino]-3,4-dihydronaphthalene-2-acetate
(44) 7-[N-(4-amidinophenyl)carbamoyl]-3,4-dihydronaphthalene-2-acetic acid
(45) methyl 7-[N-(4-amidinophenyl)carbamoyl]-3,4-dihydronaphthalene-2-acetate
(46) ethyl 7-[N-(4-amidinophenyl)carbamoyl]-3,4-dihydronaphtalene-2-acetate
(47) 7-[N-(4-amidinobenzoyl)-N-methylamino]-1,2,3,4-tetrahydronaphthalene-2-acetic acid
(48) ethyl 7-[N-(4-amidinobenzoyl)-N-methylamino]-1,2,3,4-tetrahydronaphthalene-2-acetate
(49) n-butyl 7-[N-(4-amidinobenzoyl)-N-methylamino]-1,2,3,4-tetrahydronaphthalene-2-acetate
(50) 7-[N-(4-amidinobenzoyl)-N-ethylamino]-1,2,3,4-tetrahydronaphthalene-2-acetic acid
(51) 7-[N-(4-amidinobenzoyl)-N-n-propylamino]-1,2,3,4-tetrahydronaphthalene-2-acetic acid
(52) 7-[N-(4-amidinobenzoyl)-N-isopropylamino]-1,2,3,4-tetrahydronaphthalene-2-acetic acid
(53) 7-[N-(4-amidinobenzoyl)-N-n-butylamino]-1,2,3,4-tetrahydronaphthalene-2-acetic acid
(54) 7-[N-(4-amidinobenzoyl)-N-sec-butylamino]-1,2,3,4-tetrahydronaphthalene-2-acetic acid
(55) 7-[N-(4-amidinobenzoyl)-N-isobutylamino]-1,2,3,4-tetrahydronaphthalene-2-acetic acid
(56) 7-[N-(4-amidinophenyl)-N-methylcarbamoyl]-1,2,3,4-tetrahydronaphthalene-2-acetic acid
(57) ethyl 7-[N-(4-amidinophenyl)-N-methylcarbamoyl]-1,2,3,4-tetrahydronaphthalene-2-acetic acid
(58) n-propyl 7-[N-(4-amidinophenyl)-N-methylcarbamoyl]-1,2,3,4-tetrahydronaphthalene-2-acetic acid
(59) tert-butyl 7-[N-(4-amidinophenyl)-N-methylcarbamoyl]-1,2,3,4-tetrahydronaphthalene-2-acetate
(60) 7-[N-(4-amidinophenyl)-N-ethylcarbamoyl]-1,2,3,4-tetrahydronaphthalene-2-acetic acid
(61) 7-[N-(4-amidinophenyl)-N-n-propylcarbamoyl]-1,2,3,4-tetrahydronaphthalene-2-acetic acid
(62) 7-[N-(4-amidinophenyl)-N-isopropylcarbamoyl]-1,2,3,4-tetrahydronaphthalene-2-acetic acid
(63) 7-[N-(4-amidinophenyl)-N-n-butylcarbamoyl]-1,2,3,4-tetrahydronaphthalene-2-acetic acid
(64) 7-[N-(4-amidinophenyl)-N-sec-butylcarbamoyl]-1,2,3,4-tetrahydronaphthalene-2-acetic acid
(65) 7-[N-(4-amidinophenyl)-N-isobutylcarbamoyl]-1,2,3,4-tetrahydronaphthalene-2-acetic acid
(66) 6-[N-(4-amidinobenzoyl)-N-methylamino]chroman-3-acetic acid
(67) ethyl 6-[N-(4-amidinobenzoyl)-N-methylamino]chroman-3-acetate
(68) n-propyl 6-[N-(4-amidinobenzoyl)-N-methylamino]chroman-3-acetate

(69) tert-butyl 6-[N-(4-amidinobenzoyl)-N-methylamino]chroman-3-acetate
(70) 6-[N-(4-amidinobenzoyl)-N-n-propylamino]chroman-3-acetic acid
(71) 6-[N-(4-amidinobenzoyl)-N-n-butylamino]chroman-3-acetic acid
(72) 6-[N-(4-amidinophenyl)-N-methylcarbamoyl]chroman-3-acetic acid
(73) ethyl 6-[N-(4-amidinophenyl)-N-methylcarbamoyl]chroman-3-acetate
(74) n-butyl 6-[N-(4-amidinophenyl)-N-methylcarbamoyl]chroman-3-acetate
(75) 6-[N-(4-amidinophenyl)-N-ethylcarbamoyl]chroman-3-acetic acid
(76) 6-[N-(4-amidinophenyl)-N-n-propylcarbamoyl]chroman-3-acetic acid
(77) 6-[N-(4-amidinophenyl)-N-n-butylcarbamoyl]chroman-3-acetic acid
(78) 7-[N-(4-amidinobenzoyl)-N-methylamino]-1,2,3,4-tetrahydroisoquinoline-2-acetic acid
(79) 7-[N-(4-amidinophenyl)-N-methylcarbamoyl]-1,2,3,4-tetrahydroisoquinoline-2-acetic acid
(80) 7-[(4-amidinobenzyl)oxy]-1,2,3,4-tetrahydronaphthalene-2-acetic acid
(81) methyl 7-[(4-amidinobenzyl)oxy]-1,2,3,4-tetrahydronaphthalene-2-acetate
(82) 7-[(4-amidinophenoxy)methyl]-1,2,3,4-tetrahydronaphthalene-2-acetic acid
(83) ethyl 7-[(4-amidinophenoxy)methyl]-1,2,3,4-tetrahydronaphthalene-2-acetate
(84) 7-[(4-amidinobenzyl)amino]-1,2,3,4-tetrahydronaphthalene-2-acetic acid
(85) ethyl 7-[(4-amidinobenzyl)amino]-1,2,3,4-tetrahydronaphthalene-2-acetate
(86) 7-[N-(4-amidinobenzyl)-N-methylamino]-1,2,3,4-tetrahydronaphthalene-2-acetic acid
(87) ethyl 7-[N-(4-amidinobenzyl)-N-methylamino]-1,2,3,4-tetrahydronaphthalene-2-acetate
(88) 7-[N-(4-amidinobenzyl)-N-n-butylamino]-1,2,3,4-tetrahydronaphthalene-2-acetic acid
(89) 6-[(4-amidinobenzyl)oxy]chroman-3-acetic acid
(90) ethyl 6-[(4-amidinobenzyl)oxy]chroman-3-acetate
(91) 7-[(4-amidinobenzyl)oxy]-3,4-dihydronaphthalene-2-acetic acid
(92) methyl 7-[(4-amidinobenzyl)oxy]-3,4-dihydronaphthalene-2-acetate
(93) 7-[(4-guanidinobenzoyl)amino]-1,2,3,4-tetrahydronaphthalene-2-acetic acid
(94) methyl 7-[(4-guanidinobenzoyl)amino]-1,2,3,4-tetrahydronaphthalene-2-acetate
(95) ethyl 7-[(4-guanidinobenzoyl)amino]-1,2,3,4-tetrahydronaphthalene-2-acetate
(96) n-propyl 7-[(4-guanidinobenzoyl)amino]-1,2,3,4-tetrahydronaphthalene-2-acetate
(97) tert-butyl 7-[(4-guanidinobenzoyl)amino]-1,2,3,4-tetrahydronaphthalene-2-acetate
(98) 7-[N-(4-guanidinophenyl)carbamoyl]-1,2,3,4-tetrahydronaphthalene-2-acetic acid
(99) ethyl 7-[N-(4-guanidinophenyl)carbamoyl]-1,2,3,4-tetrahydronaphthalene-2-acetate
(100) n-propyl 7-[N-(4-guanidinophenyl)carbamoyl]-1,2,3,4-tetrahydronaphthalene-2-acetate
(101) tert-butyl 7-[N-(4-guanidinophenyl)carbamoyl]-1,2,3,4-tetrahydronaphthalene-2-acetate
(102) 6-[(4-guanidinobenzoyl)amino]chroman-3-acetic acid
(103) ethyl 6-[(4-guanidinobenzoyl)amino]chroman-3-acetate
(104) n-propyl 6-[(4-guanidinobenzoyl)amino]chroman-3-acetate
(105) tert-butyl 6-[(4-guanidinobenzoyl)amino]chroman-3-acetate
(106) 6-[N-(4-guanidinophenyl)carbamoyl]chroman-3-acetic acid
(107) ethyl 6-[N-(4-guanidinophenyl)carbamoyl]chroman-3-acetate
(108) tert-butyl 6-[N-(4-guanidinophenyl)carbamoyl]chroman-3-acetate
(109) 7-[(4-guanidinobenzoyl)amino]-1,2,3,4-tetrahydroisoquinoline-2-acetic acid
(110) ethyl 7-[(4-guanidinobenzoyl)amino]-1,2,3,4-tetrahydroisoquinoline-2-acetate
(111) 7-[N-(4-guanidinophenyl)carbamoyl]-1,2,3,4-tetrahydroisoquinoline-2-acetic acid
(112) ethyl 7-[N-(4-guanidinophenyl)carbamoyl]-1,2,3,4-tetrahydroisoquinoline-2-acetate
(113) 7-[(4-guanidinobenzoyl)amino]-3,4-dihydronaphthalene-2-acetic acid
(114) 7-[(4-guanidinobenzyl)oxy]-1,2,3,4-tetrahydronaphthalene-2-acetic acid
(115) 7-[(4-guanidinobenzyl)amino]-1,2,3,4-tetrahydronaphthalene-2-acetic acid
(116) 7-[(4-guanidinophenoxy)methyl]-1,2,3,4-tetrahydronaphthalene-2-acetic acid
(117) 7-[N-(4-guanidinobenzyl)-N-methylamino]-1,2,3,4-tetrahydronaphthalene-2-acetic acid
(118) 7-[N-(4-guanidinobenzoyl)-N-methylamino]-1,2,3,4-tetrahydronaphthalene-2-acetic acid
(119) 7-[N-(4-guanidinophenyl)-N-methylcarbamoyl]-1,2,3,4-tetrahydronaphthalene-2-acetic acid
(120) 7-[N-(4-guanidinophenyl)-N-ethylcarbamoyl]-1,2,3,4-tetrahydronaphthalene-2-acetic acid
(121) 7-[N-(4-guanidinophenyl)-N-n-butylcarbamoyl]-1,2,3,4-tetrahydronaphthalene-2-acetic acid
(122) 6-[(4-guanidinobenzyl)oxy]chroman-3-acetic acid
(123) 7-[(4-aminomethylbenzoyl)amino]-1,2,3,4-tetrahydronaphthalene-2-acetic acid
(124) ethyl 7-[(4-aminomethylbenzoyl)amino]-1,2,3,4-tetrahydronaphthalene-2-acetate
(125) 7-[N-(4-aminomethylphenyl)carbamoyl]-1,2,3,4-tetrahydronaphthalene-2-acetic acid
(126) 6-[(4-aminomethylbenzoyl)amino]chroman-3-acetic acid
(127) 7-[(4-aminomethylbenzoyl)amino]-3,4-dihydronaphthalene-2-acetic acid
(128) 7-[(4-aminomethylbenzoyl)amino]-1,2,3,4-tetrahydroisoquinoline-2-acetic acid
(129) 7-[(4-aminomethylbenzyl)oxy]-1,2,3,4-tetrahydronaphthalene-2-acetic acid
(130) 7-[(4-aminomethylbenzyl)amino]-1,2,3,4-tetrahydronaphthalene-2-acetic acid
(131) 7-[(4-aminomethylphenoxy)methyl]-1,2,3,4-tetrahydronaphthalene-2-acetic acid
(132) 6-[(4-aminomethylbenzyl)oxy]chroman-3-acetic acid In the preferred compounds which are represented by the formula (1) in the invention, A is an amidino group; B is -CH$_2$O-, -OCH$_2$-, -CH$_2$N(R$^1$)-, -N(R$^1$)CH$_2$-, -CON(R$^1$)-, or -N(R$^1$)CO-, wherein R$^1$ is the same as above; W-X is -CH$_2$-CH-, -CH$_2$-N- or -CH=C-; Y is -CH$_2$- or -O-; and Z is a hydrogen atom or an alkyl group having 1–4 carbon atoms.

In the more preferred compounds which are represented by the formula (1) in the invention, A is an amidino group; B is -CON(R$^1$)- or -N(R$^1$)CO-, wherein R$^1$ is the same as above; W-X is -CH$_2$-CH=, or -CH$_2$-N=; Y is -CH$_2$- or -O-; and Z is a hydrogen atom or an alkyl group having 1–4 carbon atoms.

In the still more preferred compounds which are represented by the formula (1) in the invention, A is an amidino group; B is -CON(R¹)- or -N(R¹)CO-, wherein R¹ is a hydrogen atom or a methyl group; W-X is -CH₂-CH= or -CH₂-N=; Y is -CH₂- or -O-; and Z is a hydrogen atom or an alkyl group having 1–4 carbon atoms.

Exemplary compounds which are more preferred in the formula (1) of the invention are 7-[(4-amidinobenzoyl) amino]-1,2,3,4-tetrahydronaphthalene-2-acetic acid, 7-[N-(4-amidinophenyl)carbamoyl]-1,2,3,4-tetrahydronaphthalene-2-acetic acid, 6-[(4-amidinobenzoyl) amino]chroman-3-acetic acid, or 7-[(4-amidinobenzoyl) amino]-1,2,3,4-tetrahydroisoquinoline-2-acetic acid. Exemplary compounds which are most preferred are 7-[(4-amidinobenzoyl)amino]-1,2,3,4-tetrahydronaphthalene-2-acetic acid, 7-[N-(4-amidinophenyl)carbamoyl]-1,2,3,4-tetrahydronaphthalene-2-acetic acid, or 6-[(4-amidinobenzoyl)amino]chroman-3-acetic acid.

When an asymetric carbon atom is present in the molecule of the compound represented by the formula (1) in the invention, both R- and S-configurations of the optical isomers regarding the asymetric carbon atom are included in the scope of the invention.

Further, salts of the compound represented by the formula (1) in the invention can also be exemplified as specific compounds of the invention. Salts of the compound represented by the formula (1) include, for example, hydrochloride, hydrobromide, sulfate, nitrate, phosphate and salts of other inorganic acid; acetate, tartrate, citrate, fumarate, maleate, toluenesulfonate, methanesulfonate and salts of other organic acid; and when Z is a hydrogen atom, sodium salt, potassium salt, calcium salt, aluminum salt and other metal salts; and a salt with ammonia, primary amine such as methylamine, secondary amine such as dimethylamine, tertiary amine such as triethylamine and other organic bases. All of these salts can be pharmacologically admitted.

In the case of preparing the compound represented by the formula (1) wherein A is an amidino group, the compound represented by the formula (2) in the invention can be used with particular effect as an intermediate of synthesis.

Specific examples of the compound will be illustrated below as the compound numbers 133–164. However, the scope of the invention is not limited by these compounds. The compound number will be referred to in the below described examples.

(133) ethyl 7-[(4-cyanobenzoyl)amino]-1,2,3,4-tetrahydronaphthalene-2-acetate
(134) ethyl 7-[[4-(ethoxyiminomethyl)benzoyl]amino]-1,2,3,4-tetrahydronaphthalene-2-acetate
(135) n-propyl 7-[[4-(n-propoxyiminomethyl)benzoyl] amino]-1,2,3,4-tetrahydronaphthalene-2-acetate
(136) n-butyl 7-[[4-(n-butoxyiminomethyl)benzoyl]amino]-1,2,3,4-tetrahydronaphthalene-2-acetate
(137) ethyl 7-[N-(4-cyanophenyl)carbamoyl]-1,2,3,4-tetrahydronaphthalene-2-acetate
(138) tert-butyl 7-[N-(4-cyanophenyl)carbamoyl]-1,2,3,4-tetrahydronaphthalene-2-acetate
(139) ethyl 7-[N-[4-(ethoxyiminomethyl)phenyl] carbamoyl]-1,2,3,4-tetrahydronaphthalene-2-acetate
(140) n-butyl 7-[N-[4-(n-butoxyiminomethyl)phenyl] carbamoyl]-1,2,3,4-tetrahydronaphthalene-2-acetate
(141) ethyl 6-[(4-cyanobenzoyl)amino]chroman-3-acetate
(142) ethyl 6-[[4-(ethoxyiminomethyl)benzoyl]amino] chroman-3-acetate
(143) ethyl 6-[N-(4-cyanophenyl)carbamoyl]chroman-3-acetate
(144) ethyl 6-[N-[4-(ethoxyiminomethyl)phenyl] carbamoyl]chroman-3-acetate
(145) ethyl 7-[(4-cyanobenzoyl)amino]-1,2,3,4-tetrahydroisoquinoline-2-acetate
(146) ethyl 7-[[4-(ethoxyiminomethyl)benzoyl]amino]-1,2,3,4-tetrahydroisoquinoline-2-acetate
(147) n-butyl 7-[[4-(n-buthoxyiminomethyl)benzoyl]amino]-1,2,3,4-tetrahydroisoquinoline-2-acetate
(148) tert-butyl 7-[N-(4-cyanophenyl)carbomoyl]-1,2,3,4-tetrahydroisoquinoline-2-acetate
(149) ethyl 7-[N-[4-(ethoxyiminomethyl)phenyl] carbomoyl]-1,2,3,4-tetrahydroisoquinoline-2-acetate
(150) ethyl 7-[N-(4-cyanobenzoyl)-N-methylamino]-1,2,3,4-tetrahydronaphthalene-2-acetate
(151) ethyl 7-[N-[4-(ethoxyiminomethyl)benzoyl]-N-methylamino]-1,2,3,4-tetrahydronaphthalene-2-acetate
(152) tert-butyl 7-[N-(4-cyanophenyl)-N-methylcarbamoyl]-1,2,3,4-tetrahydronaphthalene-2-acetate
(153) ethyl 7-[N-[4-(ethoxyiminomethyl)phenyl]-N-methylcarbamoyl]-1,2,3,4-tetrahydronaphthalene-2-acetate
(154) ethyl 7-[N-(4-cyanophenyl)-N-n-butylcarbamoyl]-1,2,3,4-tetrahydronaphthalene-2-acetate
(155) ethyl 7-[N-[4-(ethoxyiminomethyl)phenyl]-N-n-butylcarbamoyl]-1,2,3,4-tetrahydronaphthalene-2-acetate
(156) methyl 7-[(4-cyanobenzyl)oxy]-1,2,3,4-tetrahydronaphthalene-2-acetate
(157) methyl 7-[[4-(methoxyiminomethyl)benzyl]oxy]-1,2,3,4-tetrahydronaphthalene-2-acetate
(158) ethyl 7-[[4-(ethoxyiminomethyl)benzyl]oxy]-1,2,3,4-tetrahydronaphthalene-2-acetate
(159) ethyl 7-[(4-cyanophenoxy)methyl]-1,2,3,4-tetrahydronaphthalene-2-acetate
(160) ethyl 7-[[4-(ethoxyiminomethyl)phenoxy]methyl]-1,2,3,4-tetrahydronaphthalene-2-acetate
(161) ethyl 6-[(4-cyanobenzyl)oxy]chroman-3-acetate
(162) ethyl 6-[[(4-(ethoxyiminomethyl)benzyl]oxy] chroman-3-acetate
(163) methyl 7-[(4-cyanobenzyl)oxy]-3,4-dihydronaphthalene-2-acetate
(164) methyl 7-[[4-(methoxyiminomethyl)benzyl]oxy]-3,4-dihydronaphthalene-2-acetate Further, in the intermediate compounds represented by the formula (2) in the invention, when an asymetric carbon atom is present in the molecule, both R- and S- configurations of the optical isomers regarding the assymetric carbon atom are also included in the scope of the invention. Salts of the intermediate compound can also be exemplified as a specific compound of the invention. These salts include, for example, hydrochloride, hydrobromide, sulfate, nitrate, phosphate and salts of other inorganic acid; and acetate, tartrate, citrate, fumarate, maleate, toluenesulfonate, methanesulfonate, and salts of other organic acid. All of these salts can be pharmacologically admitted.

The compound represented by the formula (1) in the invention can be prepared, for example, by the following processes.

Process (a)

A process for carrying out a condensation reaction of the compound represented by the formula (3):

(3)

wherein A is the same as above, and the compound represented by the formula (4):

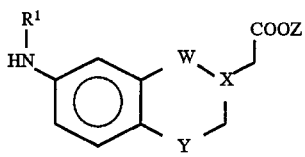 (4)

wherein W-X, Y, Z and R¹ are the same as above. Alternatively, a process for carrying out a condensation reaction of the compound represented by the formula (5):

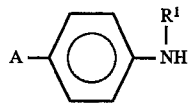 (5)

wherein A and R¹ are the same as above, and the compound represented by the formula (6):

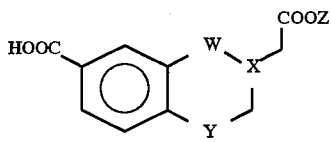 (6)

wherein W-X, Y and Z are the same as above.

Process (b)

A process for carrying out a condensation reaction of the compound represented by the formula (7):

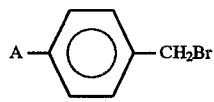 (7)

wherein A is the same as above, and the compound represented by the formula (8):

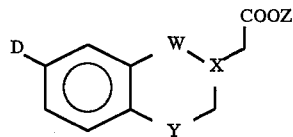 (8)

wherein W-X, Y and Z are the same as above and D is -OH or -N(R¹)H, wherein R¹ is the same as above. Alternatively, a process for carrying out a condensation reaction of the compound represented by the formula (9):

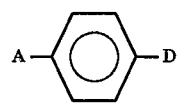 (9)

wherein A and D are the same as above, and the compound represented by the formula (10):

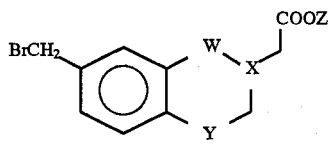 (10)

wherein W-X, Y and Z are the same as above.

Process (c)

A process for carrying out a condensation reaction of the compound represented by the formula (11):

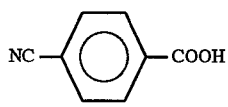 (11)

and the compound by the formula (4), or a condensation reaction of the compound represented by the formula (12):

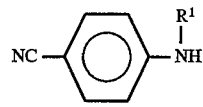 (12)

wherein R¹ is the same as above, and the compound represented by the formula (6), or a condensation reaction of the compound represented by the formula (13):

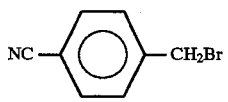 (13)

and the compound represented by the formula (8), or a condensation reaction of the compound represented by the formula (14):

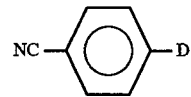 (14)

wherein D is the same as above, and the compound represented by the formula (10), to obtain the compound represented by the formula (15):

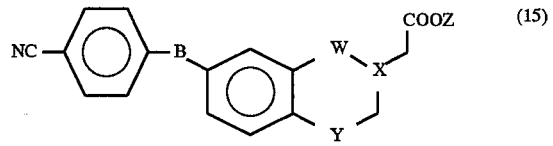 (15)

wherein B, W-X, Y and Z are the same as above, and for converting the cyano group of the compound represented by the formula (15) to an amidino group by a known process.

Process (d)

A process for carrying out a condensation reaction of the compound represented by the formula (16):

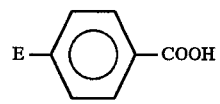 (16)

wherein E is an amino group protected by a tert-butoxycarbonyl group or a benzyloxycarbonyl group, and the compound represented by the formula (4), or a condensation reaction of the compound represented by the formula (17):

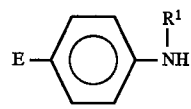 (17)

wherein E and R¹ are the same as above, and the compound represented by the formula (6), or a condensation reaction of the compound represented by the formula (18):

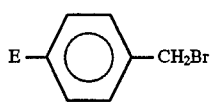

(18)

wherein E is the same as above, and the compound represented by the formula (8), or a condensation reaction of the compound represented by the formula (19):

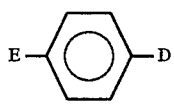

(19)

wherein E and D are the same as above, and the compound represented by the formula (10), to obtain the compound represented by the formula (20):

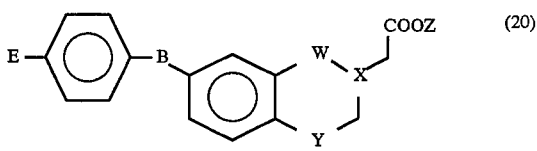

(20)

wherein E, B, W-X, Y and Z are the same as above, and to give the compound represented by the formula (21):

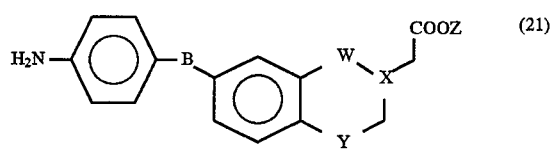

(21)

wherein B, W-X, Y and Z are the same as above, by subjecting the compound represented by the formula (20) to a treatment with an acid including trifluoroacetic acid and hydrogen chloride or a catalytic hydrogenation reaction in the presence of a catalyst such as Pd or Pt, and for converting the amino group of the compound represented by the formula (21) to a guanidino group by a known process.

The compound represented by the formula (2) can also be prepared by the process (c) above or a process described below.

Process (e)

A process for carrying out a condensation reaction of the compound represented by the formula (22):

(22)

and the compound represented by the formula (4), or a condensation reaction of the compound represented by the formula (23):

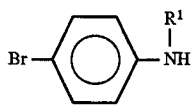

(23)

wherein $R^1$ is the same as above, and the compound represented by the formula (6), or a condensation reaction of the compound represented by the formula (24):

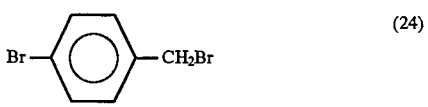

(24)

and the compound represented by the formula (8), or a condensation reaction of the compound represented by the formula (25):

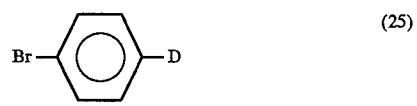

(25)

wherein D is the same as above, and the compound represented by the formula (10), to obtain the compound represented by the formula (26):

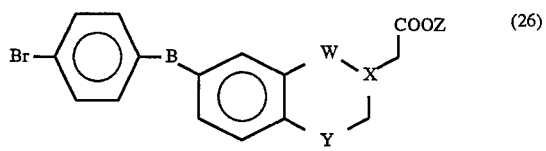

(26)

wherein B, W-X, Y and Z are the same as above, and for converting the bromine group of the compound represented by the formula (26) to a cyano group by known processes.

Process (f)

A process for converting the cyano group of the compound represented by the formula (15) to HN=C(OR²)-, wherein $R^2$ is the same as above, by known processes.

The condensation reaction in the process (a) can be carried out by utilizing the amide forming reaction in a common peptide. For example, the condensation can be carried out by using a peptide forming reagent such as dicyclohexylcarbodiimide, N,N-carbonyldiimidazole, diphenylphosphoryl azide and diethyl phosphorocyanidate, or by converting the carboxyl group to active ester, mixed anhydride or acid chloride and then reacting with the amino group. In the condensation reaction, the amidino group, guanidino group, or amino group preferably presents in the form of a salt of inorganic acid such as hydrogen chloride, hydrogen bromide and sulfuric acid, or in the state protected with a tert-butoxycarbonyl group or a benzyloxycarbonyl group. In any cases above, the condensation reaction can be accelerated by addition of a base, preferably an organic base, for example, triethylamine, N-methylpiperidine and 4-dimethylaminopyridine. The reaction temperature is usually –20° to 50° C., preferably 0° C. to room temperature. Commonly used solvents include, for example, dioxane, tetrahydrofuran, acetonitrile, N,N-dimethylformamide, chloroform and methylene chloride. These solvents can be used singly or as a mixture.

The condensation reaction in the process (b) can be carried out by known processes in the presence of a base, for example, sodium carbonate, sodium alkoxide and sodium hydride. Methanol, ethanol, 2-butanone, N,N-dimethylformamide and other solvents can be used singly or as a mixture. The reaction temperature is usually room temperature to 100° C., preferably 50° to 70° C . In the processes (a) and (b), Z is preferably an alkyl group of 1 to 4 carbon atoms.

The condensation reaction in the process (c) can be carried out by conforming to the process (a) or process (b).

Conversion of the cyano group to the amidino group can be carried out by known processes, for example, the cyano group is converted to imidate represented by the formula HN=C(OR²)-, wherein $R^2$ is the same as above, by introducing hydrogen chloride gas in a solvent such as ethanol and by reacting the resultant intermediate with ammonium acetate or ammonium chloride in an ethanol solvent. The reaction temperature is usually –20° to 50° C., preferably 0° to 20° C.

The condensation reaction in the process (d) can be carried out by conforming to the process (a) or process (b).

Conversion of the amino group to the guanidino group can be carried out by known processes, for example, by reacting the amino compound of the formula (21) with S-methylisothiourea sulfate in the presence of a base such as sodium carbonate and sodium hydroxide. Methanol, ethanol, dioxane, N,N-dimethylformamide and other solvents can be used singly or as a mixture. The reaction temperature is usually room temperature to 100° C., preferably 40° to 70° C.

The condensation reaction in the process (e) can be carried out by a process conformed to the process (a) or process (b).

Conversion of the bromine group to the cyano group can be carried out by known processes, for example, by reacting cuprous cyanide in a single solvent or a solvent mixture selected from pyridine, quinoline, N,N-dimethylformamide and N-methylpyrrolidone. The reaction temperature is usually 100° to 250° C., preferably 150° to 200° C.

In the process (f), conversion of the cyano group to the imidate group represented by $HN=C(OR^2)-$, wherein $R^2$ is the same as above, can be carried out by known processes, for example, by reacting hydrogen chloride gas in a solvent such as methanol or ethanol. The reaction temperature is usually −20° to 50° C., preferably 0° C. to room temperature. Alternatively, the reaction can be carried out by reacting sodium alkoxide in a solvent such as methanol or ethanol. The reaction temperature is usually −50° to 100° C., preferably room temperature to 50° C.

When Z is an alkyl group having 1 to 4 carbon atoms in the compound represented by the formula (1) of the invention, Z can be removed by known processes. For example, the compound having a methyl ester group or ethyl ester group can be converted to a carboxylic acid salt or free carboxylic acid by hydrolyzing with a base such an aqueous or alcoholic sodium hydroxide or by treating with an acid such as hydrochloric acid or acetic acid, respectively. The salt of the compound represented by the formula (1) can be obtained in the course of the process for preparing the compound of the formula (1) or by adding acid, alkali or base, when necessary.

The resultant compound represented by the formula (1) in the invention can be isolated from the reaction mixture by common purification methods, for example, extraction, concentration, neutralization, filtration, recrystallization and column chromatography.

The compound and its salt which are represented by the formula (1) in the invention are platelet aggregation inhibitors having GP II b/III a antagonism and inhibit formation of platelet-rich thrombus. Consequently, the compound and its salt are useful for prevention and remedy of peripheral circulatory impairments such as asterioscherosis obliterans, thromboangiitis obliterans (Buerger disease), Raynaud disease, diabetic complication e.g. diabetic retinopathy and diabetic nephropathy, vein thrombosis e.g. deep vein thrombosis, ischemic cardiac disease such as angina pectoris, e.g., stable angina pectoris and unstable angina pectoris including impending infarction, cardiac infarction, e.g., acute myocardial infarction, and coronary thrombosis, ischemic brain disease such as cerebral infarction, e.g., cerebral thrombosis and cerebral embolism, transient cerebral ischemic attack (TIA), and cerebrovascular contraction after bleeding, e.g., cerebrovascular twitch after subarachnoid hemorrhage, angiopulmonary impairment, e.g. pulmonary thrombosis and pulmonary emboism, arterial thrombus and arterial sclerosis. Further, the compound and its salt are useful for prevention of restenosis and reocclusion after percutaneous transluminal coronary angioplasty (PTCA) and percutaneous transluminal coronary recanalization (PTCR), prevention of reocclusion after administration of a tissue plasminogen activator (tPA), prevention of thrombocytopenia caused by dialysis, and prevention of thrombus formation due to artificial blood vessels and artificial organs. They are also useful for the prevention and remedy of disseminated intravascular coagulation syndrome (DIC) and inflammation, e.g., nephritis, an inhibitor of cancer metastasis, and the prevention and remedy of immunological disease. Furthermore, the compound represented by the formula (1) in the invention can be used in combination with an anti-platelet drug and anti-coagulation drug such as heparin, aspirin and warfarin. The compound and its salt represented by the formula (1) in the invention led to neither toxicity nor death of a mouse when an amount exceeding the effective dose was administered.

When a composition containing the compound and its salt represented by the formula (1) as an effective ingredient is used as an inhibitor of platelet aggregation, the dose and formulation naturally differ depending upon the properties of the compound and the symptom of a patient to be administered. In the case of oral administration, 1 to 1,000 mg/day for an adult can be administered in the formulation of tablet, granule, powder, suspension and capsule. In the case of parenteral administration, 1 to 500 mg/day for an adult can be administered in the formulation of injection, suppository and isotonic liquid for infusion. Formulation can be carried out according to known methods. For example, in the case of preparing the tablet, corn starch, lactose and crystalline cellulose are used as an excipient; hydroxypropyl cellulose carboxymethyl cellulose and gum arabic are used as a binder; starch, agar and calcium carbonate are used as a disintegrator; and magnesium stearate and talc are used as a lubricant. Sugar coating, gelatin coating and other suitable coatings can be applied to the tablet, when needed. In the case of preparing the injection, the formulation can be a non-aqueous solution obtained by using cotton seed oil, corn oil, peanut oil or olive oil; an aqueous suspension or emulsion obtained by adding water in the presence of a suitable surfactant; and an aqueous solution obtained by dissolving in a physiological saline. No particular limitation is imposed upon the content of effective ingredients in a preparation. Both solid and liquid preparations have a content of 1 to 90% in general.

EXPERIMENT

The present invention will hereinafter be illustrated in detail by way of examples. However, the scope of the invention is not limited by these examples. The compound number described in parentheses after the name of the compound is the compound number exemplified in the above detailed description of the invention.

EXAMPLE 1

Synthesis of ethyl 7-[(4-cyanobenzoyl)amino]-1,2,3,
4-tetrahydronaphthalene-2-acetate (Compound No.
133)

(1-1). The raw material 7-nitro-3,4-dihydro-(1H)-2-naphthalenone was prepared according to J. Med. Chem., 32, 2128–2134 (1989).

In 100 ml of ethylene glycol dimethyl ether, 13.4 g of ethyl diethylphosphonoacetate was dissolved, 2.4 g of 60% sodium hydride was added by portions with cooling, and the mixture was stirred for an hour at room temperature. To the resulting solution, 9.5 g of 7-nitro-3,4-dihydro-(1H)-2- naphthalenon was added and stirred for 3 hours at room temperature. The reaction solution was poured into ice water, extracted with ethyl acetate and the ethyl acetate solution was dried with anhydrous magnesium sulfate. The solvent was distilled off under reduced pressure and the concentrated residue was purified by silica gel column chromatography using a mixture, ethyl acetate: n-hexane= 1:5, as a developer, 7-nitro-3,4-dihydro-(1H)-2-naphthylideneacetate thus obtained was 5.8 g.

(1-2). The compound obtained in the step (1-1) was subjected to a catalytic hydrogenation reaction with a Pd catalyst in the presence of an aqueous hydrochloric acid. In 30 ml of chloroform, 1.5 g of thus obtained ethyl 7-amino-1,2,3,4-tetrahydronaphthalene-2-acetate hydrochloride and 1.1 g of 4-cyanobnzoyl chloride were suspended and 1.8 ml of triethylamine was added with cooling. The mixture was stirred for an hour at room temperature. Thereafter the chloroform layer was successively washed with a 1N aqueous hydrochloric acid solution, water, saturated aqueous sodium hydrogen carbonate solution and saturated aqueous sodium chloride solution, and dried with anhydrous magnesium sulfate. The solvent was distilled off under reduced pressure and the concentrated residue was purified by silica gel column chromatography using a mixture, ethanol: chloroform=1:50, as a developer. The entitled compound obtained was 0.89 g.

mp:122°–124° C.

$^1$HNMR(270 MHz,CDCl$_3$) δ ppm:7.96(d,2H,J=8.8 Hz), 7.79(d,2H,J=8.8 Hz), 7.36-7.29(m, 2H), 7.09(d,1H,J=8.8 Hz), 4.17(q,2H,J=7.3 Hz), 2.95-2.80(m, 3H), 2.57-2.36(m, 3H), 2.27 (br, 1H), 2.04-1.93 (m,1H), 1.57-1.36(m,1H), 1.28(t,3H,J=7.3 Hz)

EXAMPLE 2

Synthesis of ethyl 7-[[4-(ethoxyiminomethyl)benzoyl]amino]-1,2,3,4-tetrahydronaphthalene-2-acetate (Compound No. 134) hydrochloride In 20 ml of ethanol, 0.85 g of the compound obtained in the step (1-2) of Example 1 was suspended and cooled to below 0° C. Hydrogen chloride gas was passed through the solution for an hour while maintaining the temperature at 10° C. or less. Stirring was continued overnight at room temperature. After confirming disappearance of the raw material, the solvent was distilled off under reduced pressure and the residue was dried. The entitled compound obtained was 0.83 g.

mp:216°–218° C.

$^1$HNMR(270 MHz,DMSO-d$_6$) δ ppm:10.46(s,1H),8.25(d, 2H,J=8.1 Hz), 8.17(d,2H,J=8.1 Hz),7.52(m,2H),7.06(d,1H, J=8.8 Hz), 4.66(q,2H,J=7.3 Hz),4.10(q,2H,J=7.3 Hz),2.88-2.68(m,3H), 2.50-2.33(m,3H),2.12(br,1H),1.88(br,1H),1.51 (t,3H,J=7.3 Hz), 1.51-1.32(m,1H),1.23(t,3H,J=7.3 Hz)

EXAMPLE 3

Synthesis of ethyl 7-[(4-amidinobenzoyl)amino]-1,2,3,4-tetrahydronaphthalene-2-acetate (Compound No. 3) hydrochloride In 20 ml of ethanol, 0.83 g of the compound obtained in Example 2 was dissolved, 1.96 g of ammonium acetate was added and the mixture was stirred overnight at room temperature. The solvent was distilled off under reduced pressure and the concentrated residue was recrystallized from ethanol. The entitled compound thus obtained was 0.7 g.

mp:207°–210° C.

$^1$HNMR(270 MHz,DMSO-d$_6$)δ ppm:8.30(s,4H),8.08(d, 2H,J=8.8 Hz), 7.92(d,2H,J=8.8 Hz),7.50-7.48(m,2H),7.05 (d,1H,J=8.8 Hz), 4.10(q,2H,J=7.3 Hz),2.85-2.74(m,3H), 2.47-2.35(m,3H),2.14(br,1H), 1.91-1.87(m,1H),1.49-1.34 (m,1H),1.21(t,3H,J=7.3 Hz)

EXAMPLE 4

Synthesis of 7-[(4-amidinobenzoyl)amino]-1,2,3,4-tetrahydronaphthalene-2-acetic acid (Compound No. 1) hydrochloride In 10 ml of ethanol, 0.1 g of the compound obtained in Example 3 was suspended and 1.2 ml of a 2N aqueous sodium hydroxide solution was added and stirred overnight at room temperature. Most of the solvent was distilled off under reduced pressure. The concentrated residue was converted to acidic by adding a 3N aqueous hydrochloric acid solution. Formed precipitate was filtered and washed with water several times. The entitled compound thus obtained was 0.07 g.

mp:236°–238° C.

$^1$HNMR(270 MHz,TFA-d) δ ppm:8.20(d,2H,J=8.8 Hz), 8.03(d,2H,J=8.8 Hz), 7.68-7.65(m,2H),7.34(d,1H,J=8.8 Hz),3.07-2.96(m,3H), 2.69-2.59(m,3H),2.41(br,1H),2.15-2.11(m,1H),1.71-1.56(m,1H) MS:m/e=352(M$^+$+1)

EXAMPLE 5

Synthesis of tert-butyl 7-[N-(4-cyanophenyl)carbamoyl]-1,2,3,4-tetrahydronaphthalene-2-acetate (Compound No. 138)

(5-1) The raw material 7-methoxycarbonyl-3,4-dihydro-(2H)-1-naphthalenone was prepared according to Tetrahedron Lett., 33(38), 5492–5502 (1992).

In a mixture of 150 ml of methanol and 50 ml of tetrahydrofuran, 24.1 g of 7-methoxycarbonyl-3,4-dihydro-(2H)-1 -naphthalenone was dissolved and 5 g of sodium borohydride was added by portions with ice cooling. The mixture was stirred at 5° C. for an hour and successively the solvent was distilled off under reduced pressure. The concentrated residue was adjusted to pH 2 by adding a 2N aqueous hydrochloric acid solution and extracted with chloroform. The chloroform layer was dried with anhydrous magnesium sulfate. The solvent was distilled off under reduced pressure to obtain crude intermediate 7-methoxycarbonyl-1,2,3,4-tetrahydro-1-naphthol. The crude intermediate was dissolved in 150 ml of benzene, 5 g of Amberlyst 15 was added, a Dean-Stark Trap was mounted, and the mixture was refluxed by heating for 2 hours. After cooling, the reaction mixture was filtered and the solvent was distilled off under reduced pressure. The concentrated residue was purified by silica gel column chromatography using a mixture, ethyl acetate: n-hexane= 1:10, as a developer. 7-methoxycarbonyl-3,4-dihydronaphthalene thus obtained was 19.2 g.

(5-2) A chloroform solution containing 18.5 g of the compound obtained in the step (5-1) and 9.4 g of m-chloroperbenzoic acid having content of 80% was stirred for 3 hours at room temperature. The reaction was stopped by adding an aqueous sodium hydrogen carbonate solution and aqueous sodium sulfite solution to the reaction mixture, and the organic layer was extracted with chloroform. The chloroform solution was dried with anhydrous magnesium sulfate and the solvent was distilled off under reduced pressure. The crude compound thus obtained was purified by silica gel column chromatography using a mixture, n-hexane: chloroform=3:1, as a developer to give 8.42 g of 1,2-epoxy-7-methoxycarbonyl-1,2,3,4-tetrahydronaphthalene.

(5-3) In 20 ml of benzene, 1.3 g of the compound obtained in the step (5-2) was dissolved and 2.5 g zinc iodide was added. The mixture was stirred under light shield for 6 hours at room temperature. The reaction mixture was filtered, and concentrated under reduced pressure. The crude compound obtained was purified by silica gel column chromatography using a mixture, chloroform: ethyl acetate 20:1, as a developer to give 1.1 g of 7-methoxycarbonyl-3,4-dihydro-(1H)-2-naphthalenone.

(5-4) In 30 ml of toluene, 1.1 g of the compound obtained in the step (5-3) and 3.8 g of tert-butoxycarbonylmethylenetriphenylphosphorane were dissolved and refluxed for 5 hours at 100° C. The solvent was distilled off under reduced pressure. The concentrated residue was purified by silica gel column chromatography using a mixture, ethyl acetate: n-hexane=1:5, as a developer to give 0.85 g of tert butyl 7-methoxycarbonyl-1,2,3,4-tetrahydro-2-naphthylidene-acetate.

(5-5) A catalytic hydrogenation reaction in the presence of a Pd catalyst was carried out by using 0.8 g of the compound obtained in the step (5-4). Tert-butyl 7-methoxycarbonyl-1,2,3,4-tetrahydronaphthalene-2-acetate thus obtained was 0.8 g.

(5-6) The same reaction as described in Example 4 was carried out by using 0.78 g of the compound obtained in the step (5-5). Thus obtained tert-butyl 7-carboxy-1,2,3,4-tetrahydronaphthalene-2-acetate was 0.71 g.

(5-7) In 5 ml of toluene, 0.7 g of the compound obtained in the step (5-6) and 1.5 ml of oxalyl chloride were dissolved and a drop of N,N-dimethylformamide was added. The mixture was stirred for an hour at room temperature. The solvent was distilled off under reduced pressure to obtain corresponding acid chloride. Acid chloride thus obtained was dissolved in 5 ml of tetrahydrofuran, and 0.35 g of 4-aminobenzonitrile, 1 ml of pyridine and 50 mg of 4-dimethylaminopyridine were added. The mixture was stirred for 4 hours at room temperature. The reaction mixture was mixed with on aqueous sodium hydrogen carbonate solution and extracted with chloroform. The extracted chloroform solution was dried with anhydrous magnesium sulfate. The solvent was distilled off under reduced pressure to obtain crude product. The crude product was purified by silica gel column chromatography using a mixture, chloroform:ethyl acetate=5:1, as a developer to yield 0.47 g of the entitled compound.

mp:152°–154° C.

$^1$HNMR(270 MHz,CDCl$_3$) δ ppm:7.96(brs,1H),7.79(d, 2H,J=8.8 Hz), 7.65(d,2H,J=8.8 Hz),7.55-7.54(m,2H),7.20 (d,1H,J=8.1 Hz), 3.01-2.85(m,3H),2.60-2.49(m,1H),2.33-2.21(m,3H),2.04-1.95(m,1H), 1.48(s,9H),1.51-1.48(m,1H)

EXAMPLE 6

Synthesis ethyl 7-[N-(4-amidinophenyl)carbamoyl]-1,2,3,4-tetrahydronaphthalene-2-acetate (Compound No. 11) hydrochloride The same reactions as described in Example 2 and Example 3 were carried out by using 0.45 g of the compound obtained in Example 5, step (5-7) to yield 0.38 g of the entitled compound.

mp:216°–217° C.

$^1$HNMR(270 MHz,DMSO-d$_6$) δ ppm:7.97(d,2H,J=8.8 Hz), 7.81(d,2H,J=8.8 Hz),7.72-7.70(m,2H),7.20(d,1H,J=8.1 Hz), 4.13(q,2H,J=6.6 Hz),2.98-2.74(m,3H),2.60-2.50(m, 1H), 2.45(d,2H,J=7.3 Hz),2.26-2.08(m,1H),1.96-1.87(m, 1H), 1.53-1.38(m,1H),1.21(t,3H,J=6.6 Hz)

EXAMPLE 7

Synthesis of 7-[N-(4-amidinophenyl)carbamoyl]-1, 2,3,4-tetrahydronaphthalene-2-acetic acid (Compound No. 9) hydrochloride The same reaction as described in Example 4 was carried out by using 0.14 g of the compound obtained in Example 6 to yield 0.1 g of the entitled compound.

mp:above 230° C.

$^1$HNMR(270 MHz,TFA-d) δ ppm:8.00(d,2H,J=8.8 Hz), 7.93(d,2H,J=8.8 Hz), 7.68-7.65(m,2H),7.34(d,1H,J=8.8 Hz),3.14-3.00(m,3H), 2.74-2.65(m,3H),2.53-2.13(m,1H), 1.75-1.60(m,1H)

EXAMPLE 8

Synthesis of ethyl 6-[(4-cyanobenzoyl)amino] chroman-3-acetate (Compound No. 141)

(8-1) After cooling 40 ml of fuming nitric acid to –30° to –35° C., 5.8 g of 4-chromanone was added with stirring over about 30 minutes and further stirred for 30 minutes at the same temperature. The reaction mixture was successively poured into ice water and extracted with 500 ml of ethyl acetate. The organic layer was dried with anhydrous magnesium sulfate and the solvent was distilled off under reduced pressure. The crude product thus obtained was washed with a solvent mixture, n-hexane:ethyl acetate=1:1, to give 5.4 g of 6-nitro-4-chromanone.

(8-2) The same reaction as described in Example 5, step (5-1) was carried out by using 5.4 g of the compound obtained in the step (8-1) to give 4.9 g of 6-nitro-(2H)-chroman.

(8-3) The same reaction as described in Example 5, step (5-2) was carried out by using 4.9 g of the compound obtained in the step (8-2) to give 4.0 g of 3,4-epoxy-6-nitro-chroman.

(8-4) The same reaction as described in Example 5, step (5-3) was carried out by using 3.9 g of the compound obtained in the step (8-3) to give 3.5 g of 6-nitro-3-chromanone.

(8-5) The same reaction as described in Example 1, step (1-1) was carried out by using 3.5 g of the compound obtained in the step (8-4) to give 2.5 g of ethyl 6-nitro-3-chromanylidene-acetate.

(8-6) The same reaction as described in Example 1, step (1-2) was carried out by using 1.3 g of ethyl 6-aminochroman-3-acetate which was prepared by subjecting the compound obtained in the step (8-5) to catalytic hydrogenation in the presence of Pd catalyst, and 1.1 g of 4-cyanobenzoyl chloride. The entitled compound thus obtained was 0.89 g.

mp:165°–166° C.

$^1$HNMR(270 MHz,CDCl$_3$) δ ppm:7.95(d,2H,J=8.1 Hz), 7.78(d,2H,J=8.8 Hz), 7.72(d,1H,J=2.2 Hz),7.20(dd,1H,J= 8.8, 2.2 Hz),6.81(d,1H,J=8.8 Hz), 4.25-4.20(m,1H),4.15(q, 2H,J=7.3 Hz),3.94-3.86(m,1H), 3.03-2.92(m,1H),2.62-2.52 (m,2H),2.47-2.30(m,2H), 1.28(t,3H,J=7.3 Hz)

EXAMPLE 9

Synthesis of ethyl 6-[[4-(ethoxyiminomethyl) benzoyl]amino]chroman-3-acetate (Compound No. 142) hydrochloride The same reaction as described in Example 2 was carried out by using 1.0 g of the compound obtained in Example 8, step (8-6) to yield 0.9 g of the entitled compound.

mp:239°–240° C.

$^1$HNMR(270 MHz,DMSO-$d_6$) δ ppm:10.41(s,1H),8.24(d, 2H,J=8.8 Hz), 8.17(d,2H,J=8.8 Hz),7.48(m,2H),6.77(d,1H, J=8.8 Hz), 4.66(q,2H,J=7.3 Hz),4.20-4.10(m,1H),4.11(q, 2H,J=7.3 Hz),3.82(m,1H), 2.90(m,1H),2.60-2.32(m,4H), 1.51(t,3H,J=7.3 Hz),1.21(t,3H,J=7.3 Hz)

EXAMPLE 10

Synthesis of ethyl 6-[(4-amidinobenzoyl)amino]chroman-3-acetate (Compound No. 19) hydrochloride The same reaction as described in Example 3 was carried out by using 0.5 g of the compound obtained in Example 9 to yield 0.34 g of the entitled compound (amorphous).

$^1$HNMR(270 MHz,DMSO-$d_6$) δ ppm:10.26(s,1H),8.29(s, 4H), 8.10(d,2H,J=8.8 Hz),7.92(d,2H,J=8.8 Hz),7.50(s,1H), 7.45(dd,1H,J=8.8,2.2 Hz),6.74(d,1H,J=8.8 Hz),4.20-4.07 (m,3H), 3.85-3.82(m,1H),2.92-2.86(m,1H),2.55-2.33(m, 4H), 1.21(t,3H,J=7.3 Hz)

EXAMPLE 11

Synthesis of 6-[(4-amidinobenzoyl)amino]chroman-3-acetic acid (Compound No. 17) hydrochloride The same reaction as described in Example 4 was carried out by using 0.34 g of the compound obtained in Example 10 to yield 0.22 g of the entitled compound (amorphous).

$^1$HNMR(270 MHz,DMSO-$d_6$) δ ppm:10.31(s,1H),9.50 (brs,2H), 9.22(brs,2H),8.14(d,2H,J=8.8 Hz),7.94(d,2H,J= 8.8 Hz),7.50(s,1H), 7.45(dd,1H,J=8.8,2.2 Hz),6.75(d,1H,J= 8.8),4.20-4.16(m,1H), 3.85-3.78(m,1H),2.91-2.85(m,1H), 2.57-2.51(m,4H)

EXAMPLE 12

Synthesis of ethyl 7-[(4-cyanobenzoyl)amino]-1,2,3,4-tetrahydroisoquinoline-2-acetate (Compound No. 145) hydrochloride (12-1) The raw material 7-nitro-1,2,3,4-tetrahydroisoquinoline was prepared according to Heterocyclic Chemistry,22, 329 (1985).

In 20 ml of ethanol, 2.89 g of 7-nitro-1,2,3,4-tetrahydroisoquinoline was dissolved, 3.9 ml of triethylamine and 2.25 g of ethyl bromoacetate were added, and the mixture was refluxed by heating for an hour. After 1 hour, most of the solvent was distilled off under reduced pressure. The concentrated residue was extracted with ethyl acetate and dried with anhydrous magnesium sulfate. The solvent was distilled off under reduced pressure. The crude product obtained was purified by silica gel column chromatography using a mixture, ethyl acetate:n-hexane=1:3, as a developer and successively treated with a hydrochloric acid/dioxane solution to give 2.14 g of ethyl 7-nitro-1,2,3,4-tetrahydroisoquinoline-2-acetate hydrochloride.

(12-2) In 30 ml of ethanol, 2.14 g of the compound obtained in the step (12-1) was suspended and subjected to catalytic hydrogenation reaction in the presence of a Pd catalyst. Ethyl 7-amino-1,2,3,4-tetrahydroisoquinoline-2-acetate thus obtained was converted to dihydrochloride by treating with a hydrochloric acid/dioxane solution. In 30 ml of chloroform, 2.18 g of the dihydrochloride obtained and 1.41 g of 4-cyanobenzoyl chloride were suspended, and 3.2 ml of triethylamine was added with cooling. The mixture was stirred for an hour at room temperature. The chloroform layer was successively washed with water, saturated aqueous sodium hydrogen carbonate solution, and saturated sodium chloride solution and dried with anhydrous magnesium sulfate. The solvent was distilled off under reduced pressure. The crude product thus obtained was purified by silica gel column chromatography using a mixture, ethanol:chloroform=1:50, as a developer and was treated with a hydrochloric acid/dioxane solution to yield 2.24 g of the entitled compound (amorphous).

$^1$HNMR(270 MHz,DMSO-$d_6$) δ ppm:10.62(s,1H),8.14(d, 2H,J=8.8 Hz), 8.01(d,2H,J=8.8 Hz),7.75-7.63(m,2H),7.25 (d,1H,J=8.8 Hz), 4.50(brs,2H),4.35(s,2H),4.27(q,2H,J=7.3 Hz),3.50(brs,2H), 3.10(br,2H)

EXAMPLE 13

Synthesis of ethyl 7-[(4-amidinobenzoyl)amino]-1,2,3,4-tetrahydroisoquinoline-2-acetate (Compound No. 30) dihydrochloride The same reactions as described in Example 2 and 3 were carried out by using 1.0 g of the compound obtained in Example 12, step (12-2) to yield 0.7 g of the entitled compound.

mp:172°–173° C.

$^1$HNMR(270 MHz,DMSO-$d_6$) δ ppm:10.38(s,1H),8.30(s, 4H), 8.14(d,2H,J=8.8 Hz),7.94(d,2H,J=8.8 Hz),7.54(s,1H), 7.50(dd,1H,J=8.8,2.2 Hz),7.10(d,1H,J=8.8 Hz),4.13(q,2H, J=7.3 Hz), 3.70(s,2H),3.42(s,2H),2.80(s,4H),1.22(t,3H,J= 7.3 Hz)

EXAMPLE 14

Synthesis of 7-[(4-amidinobenzoyl)amino]-1,2,3,4-tetrahydroisoquinoline-2-acetic acid (Compound No. 28) dihydrochloride The same reaction as described in Example 4 was carried out by using 0.1 g of the compound obtained in Example 13 to yield 0.03 g of the entitled compound.

mp:238°–240° C. (decomposed)

$^1$HNMR(270 MHz,DMSO-$d_6$) δ ppm:10.43(s,1H),9.49 (brs,2H), 9.36(brs,2H),8.16(d,2H,J=8.8Hz),7.96(d,2H,J=8.8 Hz),7.61(s,1H), 7.55(dd,1H,J=8.8,2.2 Hz),7.12(d,2H,J=8.8 Hz),3.82(s,2H), 3.37(s,2H),2.93-2.75(m,4H)

EXAMPLE 15

Synthesis of tert-butyl 7-[N-(4-cyanophenyl)carbamoyl]-1,2,3,4-tetrahydroisoquinoline-2-acetate (Compound No. 148)

(15-1) The raw material 7-methoxyisoquinoline was prepared according to J. Org. Chem., 38(21), 3701(1973).

A mixture of 7.4 g of 7-methoxyisoquinoline and 30 g of pyridine hydrochloride was heated with stirring at 180° for 6 hours. The reaction mixture was allowed to cool, dissolved in ethyl acetate, and washed with a saturated aqueous sodium chloride solution. The solution was dried with anhydrous magnesium sulfate and the solvent was distilled off under reduced pressure to give 4.43 g of 7-hydroxyisoquinoline. The compound thus obtained was dissolved in 100 ml of methylene chloride, 5.5 ml of pyridine was added and then 6.6 ml of trifluoromethanesulfonic anhydride was dropwise added. The mixture was stirred for an hour with ice cooling. After reaction, a saturated aqueous sodium hydrogen carbonate solution was added to the reaction mixture and extracted with chloroform. The chloroform layer was dried with anhydrous magnesium sulfate and the solution was concentrated under reduced pressure. The crude product thus obtained was purified by silica gel column chromatography using a mixture, ethyl acetate:n-hexane=1:3, as a developer to give 9.18 g of trifluoromethanesulfonic acid-7-isoquinolinyl.

(15-2) In a 500 ml autoclave, 8.6 g of the compound obtained in the step (15-1), 9.0 ml of triethylamine, 1.07 g of tetrakis (triphenylphosphine)palladium and 0.38 g of 1,3-bis(diphenylphosphino)propane were dissolved in a mixture composed of 30 ml of methanol and 60 ml of N,N-dimethylformamide. After charging carbon monoxide to the pressure of 15 kg/cm², the mixture was stirred at 70° C. for 3 hours. After cooling, the reaction mixture was concentrated under reduced pressure and purified by silica gel column chromatography using a mixture, chloroform:ethyl acetate=10:1, as a developer to give 5.39 g of 7-methoxycarbonylisoquinoline.

(15-3) In 50 ml of acetonitrile, 5.39 g of the compound obtained in the step (15-2) and 6.7 g tert-butyl bromoacetate was dissolved and the mixture was refluxed by heating for 6 hours. After cooling, separated precipitate was filtered and washed with isopropyl ether. The solid obtained was dried under reduced pressure to give 8.75 g of 7-methoxycarbonyl-2-tert-butoxycarbonylmethyl-isoquinolinium bromide.

(15-4) In 60 ml of methanol, 7.3 g of the compound obtained in the step (15-3) was suspended and cooled with ice. To the suspension, 1.45 g of sodium borohydride was added by portions and stirred for 30 minutes with ice cooling. Thereafter 1 ml of water was added and the solvent was distilled off under reduced pressure. The residue was extracted with a mixture composed of saturated aqueous sodium chloride solution and chloroform, and the organic layer was dried with anhydrous magnesium sulfate. The solvent was distilled off under reduced pressure. The crude product obtained was purified by silica gel column chromatography using a mixture, chloroform: ethyl acetate=20:1, to give 3.4 g of tert-butyl 7-methoxycarbonyl-1,2,3,4-tetrahydroisoquinoline-2-acetate.

(15-5) In 30 ml of methanol, 2.4 g of the compound obtained in the step (15-4) was dissolved and 20 ml of an aqueous solution containing 1.1 g of barium hydroxide 8 hydrate was added with ice cooling. The mixture was stirred for 7 hours at room temperature. Methanol was distilled off under reduced pressure. The residue was adjusted to pH 4.5 with an 1N aqueous hydrochloric acid solution and concentrated under reduced pressure. The crude product obtained was purified by ODS column chromatography using a mixture, methanol:water=1:2, as a developer to give 0.9 g of tert-butyl 7-carboxy-1,2,3,4-tetrahydroisoquinoline-2-acetate.

(15-6) In a solvent mixture composed of 20 ml of methylene chloride and 10 ml of tetrahydrofuran, 0.84 g of the compound obtained in the step (15-5), 0.35 g of 4-aminobenzonitrile and 0.41 g of 1-hydroxybenzotriazole monohydrate were dissolved and cooled with ice. To the solution, 0.61 g of dicyclohexylcarbodiimide was added and stirred for an hour with ice cooling and overnight at room temperature. Formed dicyclohexylurea was filtered and the filtrate was concentrated. The crude product thus obtained was purified by silica gel column chromatography using a mixture, chloroform:methanol=30:1, as a developer to yield 0.54 g of the entitled compound.

mp:180° C. (decomposed) ¹HNMR(270 MHz,CDCl₃) δ ppm:7.85–7.70(m,2H),7.65(d,2H,J=8.8 Hz), 7.33(d,2H,J= 8.8 Hz),7.15(d,1H,J=2.2 Hz),3.83(s,2H),3.33(s,2H), 2.99-2.86(m,4H),1.50(s,9H)

EXAMPLE 16

Synthesis of 7-[N-(4-amidinophenyl)carbamoyl]-1, 2,3,4-tetrahydroisoquinoline-2-acetic acid (Compound No. 36) dihydrochloride The same reactions as described in Example 2 and Example 3 were carried out by using 0.5 g of the compound obtained in Example 15, step (15-6) to give ethyl 7-[N-(4-amidinophenyl)carbamoyl]-1,2,3,4-tetrahydroisoquinoline-2-acetate dihydrochloride. The compound obtained was dissolved in 20 ml of ethanol without further purification and the same reaction as described in Example 4 was carried out. The product obtained was purified by ODS column chromatography using a mixture, water: methanol=2:1, as a developer to yield 0.12 g of the entitled compound.

mp:above 230° C.

¹HNMR(270 MHz,DMSO-d₆) δ ppm:10.45(s,1H),9.46 (brs,2H), 9.35(brs,2H),7.64(d,2H,J=8.8 Hz),7.32(d,2H,J= 8.8 Hz), 7.20-7.18(m,2H),7.15(d,1H,J=2.2 Hz),3.83(s,2H), 3.33(s,2H), 2.99-2.86(m,4H)

EXAMPLE 17

Synthesis of ethyl 7-[N-(4-cyanobenzoyl)-N-methylamino]-1,2,3,4-tetrahydronaphthalene-2-acetate (Compound No. 150)

(17-1) In 10 ml of N,N-dimethylformamide, 0.67 g of ethyl 7-[N-(t-butoxycarbonyl)amino]-1,2,3,4-tetrahydronaphthalene-2-acetate was dissolved and 0.096 g of 60% sodium hydride was added under cooling and stirred for 5 minutes at room temperature. To the mixture, 0.57 g of methyl iodide was dropwise added and allowed to stand overnight at room temperature. The reaction mixture was concentrated under reduced pressure and the concentrated residue was extracted with ethyl acetate. The ethyl acetate solution was dried with anhydrous magnesium sulfate. The solvent was distilled off under reduced pressure, then the obtained crude product was purified by silica gel column chromatography using a mixture, ethyl acetate:n-hexane= 1:10, as a developer to give 0.67 g of ethyl 7-[N-(t-butoxycarbonyl)-N-methylamino]-1,2,3,4-tetrahydronaphthalene-2-acetate.

(17-2) Hydrochloride was prepared by treating the compound obtained in the step (17-1) with a hydrochloric acid/dioxane solution. The same reaction as described in Example 1, step (1-2) was carried out by using 0.56 g of the hydrochloride obtained to yield 0.5 g of the oily entitled compound.

¹HNMR(270 MHz,CDCl₃) δ ppm:7.62(d,2H,J=8.8 Hz), 7.40(d,2H,J=8.8 Hz), 6.95-6.83(m,3H),4.07(q,2H,J=7.3 Hz),3.33(s,3H),2.74-2.65(m,3H), 2.45-2.22(m,3H),2.08-2.04(m,1H),1.84-1.80(m,1H),1.41-1.37(m,1H), 1.19(t,3H, J=7.3 Hz)

EXAMPLE 18

Synthesis of ethyl 7-[N-(4-amidinobenzoyl)-N-methylamino]-1,2,3,4-tetrahydronaphthalene-2-acetate (Compound No. 48) hydrochloride The same reactions as described in Example 2 and Example 3 were carried out by using 0.5 g of the compound obtained in Example 17, step (17-2) to yield 0.37 g of the entitled compound.

mp:188°–189° C.

¹HNMR(270 MHz,DMSO-$d_6$) δ ppm: 8.29(s,4H),7.63(d, 2H,J=8.8 Hz), 7.41(d,2H,J=8.8 Hz),6.95-6.83(m,3H),4.07 (q,2H,J=7.3 Hz), 3.33(s,3H),2.74-2.68(m,3H),2.45-2.27(m,3H),2.08-2.04(m,1H), 1.84-1.80(m,1H),1.41-1.37(m,1H), 1.19(t,3H,J=7.3 Hz)

EXAMPLE 19

Synthesis of 7-[N-(4-amidinobenzoyl)-N-methylamino]-1,2,3,4-tetrahydronaphthalene-2-acetic acid (Compound No. 47) hydrochloride The same reaction as described in Example 4 was carried out by using 0.1 g of the compound obtained in Example 18 to yield 0.07 g of the entitled compound.

mp:above 250° C.

¹HNMR(270 MHz,DMSO-$d_6$) δ ppm:9.30(brs,2H),9.07 (brs,2H), 7.66(d,2H,J=8.8 Hz),7.42(d,2H,J=8.8 Hz),6.90-6.83(m,3H),3.33(s,3H), 2.75-2.60(m,3H),2.45-2.25(m,3H), 2.09-2.04(m,1H),1.88-1.80(m,1H), 1.42-1.37(m,1H)

EXAMPLE 20

Synthesis of tert-butyl 7-[N-(4-cyanophenyl)-N-methylcarbamoyl]-1,2,3,4-tetrahydronaphthalene-2-acetate (Compound No. 152)

(20-1) A solution containing 2.0 g of 4-aminobenzonitrile and 2.7 ml of pyridine in 20 ml of methylene chloride was cooled with ice and 2.8 ml of trifluoroacetic anhydride was dropwise added over 2 minutes. The reaction mixture was stirred for an hour. Thereafter, a saturated aqueous sodium hydrogen carbonate solution was added to the reaction mixture and the reaction mixture was extracted with chloroform. The organic layer was dried with anhydrous magnesium sulfate and concentrated under reduced pressure to give 3.85 g of N-(4-cyanophenyl)-α, α, α-trifluoroacetoamide. The compound obtained was dissolved in 40 ml of 2-butanone, 3.3 g of potassium hydroxide powder and 3.7 ml of methyl iodide were added, and the mixture was refluxed by heating for an hour. After allowing to cool, the solvent was distilled off under reduced pressure to obtain oily substance. The oily substance was suspended in 40 ml of water and stirred at 80° C. for an hour. After allowing to cool, the reaction mixture was filtered with Celite and the filtrate was concentrated under reduced pressure. The crude product obtained was purified by silica gel column chromatography using a mixture, ethyl acetate:n-hexane=1:3, as a developer to give 1.82 g of 4-methylaminobenzonitirile.

(20-2) In 5 ml of toluene, 1.0 g of the compound obtained in Example 5, step (5-6) was suspended and 0.6 ml of oxalyl chloride and a drop of N,N-dimethylformamide were added. The mixture was stirred for an hour at room temperature. After finishing the reaction, the reaction mixture was concentrated under reduced pressure to obtain corresponding acid chloride. The acid chloride was dissolved in 5 ml of chloroform and dropwise added with ice cooling to 10 ml of a chloroform solution containing 0.68 g of the compound obtained in step (20-1) and 0.63 g of 4-dimethylaminopyridine. The mixture was stirred overnight at room temperature, successively mixed with a saturated aqueous sodium hydrogen carbonate solution, and extracted with chloroform. The chloroform solution was dried with anhydrous magnesium sulfate and concentrated under reduced pressure. The crude product obtained was purified by silica gel column chromatography using a mixture, ethyl acetate:n-hexane=1:2, as a developer, to yield 0.96 g of the oily entitled compound.

¹HNMR(270 MHz,CDCl₃) δ ppm:7.53(dt,2H,J=8.8,2.2 Hz), 7.14(dt,2H,J=8.8,2.2 Hz),7.11(s,1H),6.90(d,1H,J=8.8 Hz), 6.86(d,1H,J=8.8 Hz),3.50(s,3H),2.80-2.73(m,3H),2.43-1.90(m,5H), 1.46(s,9H),1.45-1.36(m,1H)

EXAMPLE 21

Synthesis of ethyl 7-[N-(4-amidinophenyl)-N-methylcarbamoyl]-1,2,3,4-tetrahydronaphthalene-2-acetate (Compound No. 57) hydrochloride The same reactions as described in Example 2 and Example 3 were carried out by using 0.96 g of the compound obtained in Example 20, step (20-2) to yield 1.03 g of the entitled compound.

mp:178°–180° C. (decomposed)

¹HNMR(270 MHz,DMSO-$d_6$) δ ppm:7.72(d,2H,J=8.1 Hz), 7.37(d,2H,J=8.1 Hz),7.08(s,1H),6.96(d,1H,J=8.1 Hz), 6.91(d,1H,J=8.1 Hz),4.07(q,2H,J=7.3 Hz),3.38(s,3H), 2.75-1.26(m,9H),1.18(t,3H,J=7.3 Hz)

EXAMPLE 22

Synthesis of ethyl 7-[N-(4-amidinophenyl)-N-methylcarbamoyl]-1,2,3,4-tetrahydronaphthalene-2-acetic acid (Compound No. 56) hydrochloride The same reaction as described in Example 4 was carried out by using 0.3 g of the compound obtained in Example 21 to yield 0.17 g of the entitled compound.

mp:200° C. (decomposed) ¹HNMR(270 MHz,DMSO-$d_6$) δ ppm:7.69(d,2H,J=8.1 Hz), 7.33(d,2H,J=8.1 Hz),7.08(s,1H),6.96(d,1H,J=8.1 Hz), 6.91(d,1H,J=8.8 Hz),3.35(s,3H), 2.82-1.21(m, 9H)

EXAMPLE 23

Synthesis of methyl 7-[(4-cyanobenzyl)oxy]-1,2,3,4-tetrahydronaphthalene-2-acetate (Compound No. 156)

The raw material methyl 7-hydroxy-1,2,3,4-tetrahydronaphthalene-2-acetate was prepared according to HELVETICA CHIMICA ACTA, 71, 1156 (1988).

In 50 ml of 2-butanone, 1.2 g of methyl 7-hydroxy-1,2,3,4-tetrahydronaphthalene-2-acetate and 1.60 g of 4-cyanobenzyl bromide were dissolved, 1.51 g of potassium carbonate was added, and the mixture was refluxed by heating for 12 hours. Most of the solvent was distilled off under reduced pressure. The concentrated residue was mixed with water and extracted with ethyl acetate. The organic layer was dried with anhydrous magnesium sulfate and the solvent was distilled off under reduced pressure. The concentrated residue was purified by silica gel column chromatography using a mixture, ethyl acetate:n-hexane=1:3, as a developer to yield 1.7 g of the entitled compound.

mp:120°–122° C.

¹HNMR(270 MHz,CDCl₃) δ ppm:7.65(d,2H,J=8.8 Hz), 7.44(d,2H,J=8.8 Hz), 6.75(dd,1H,J=8.8,2.2 Hz),6.70(s,1H), 5.18(s,2H),3.60(s,3H), 2.75-2.60(m,3H),2.45-2.25(m,3H), 2.09-2.04(m,1H),1.88-1.80(m,1H), 1.42-1.30(m,1H)

EXAMPLE 24

Synthesis of methyl 7-[(4-amidinobenzyl)oxy]-1,2,3,4-tetrahydronaphthalene-2-acetate (Compound No. 81) hydrochloride In 30 ml of methanol, 1.7 g of the compound in Example 23 was dissolved and cooled to 0° C. or below. Hydrogen chloride gas was ventilated through the solution for 1 hour so as to maintain the reaction temperature 10° C. or less. The mixture was stirred at room temperature. After confirming disappearance of the raw material, methanol was distilled off under reduced pressure. The concentrated residue was dissolved in 30 ml of methanol, 1.96 g of ammonium acetate was added, and the mixture was stirred overnight at room temperature. The solvent was distilled off under reduced pressure, and the concentrated residue was purified by silica gel column chromatography using a mixture, methanol:chloroform:acetic acid=1:10:0.5, as a developer to yield 1.3 g of the entitled compound.

mp:177°–179° C.

$^1$HNMR(270 MHz,DMSO-d$_6$) δ ppm:9.34(brs,2H),9.02 (brs,2H), 7.82(d,2H,J=8.8 Hz),7.65(d,2H,J=8.8 Hz),6.97(d, 1H,J=8.1 Hz), 6.75(dd,1H,J=8.1,2.2 Hz),6.70(s,1H),5.18(s, 2H),3.61(s,3H),2.81-2.69(m,3H),2.44-2.35(m,3H),2.07-2.00(m,1H),1.87-1.83(m,1H), 1.45-1.30(m,1H)

EXAMPLE 25

Synthesis of 7-[(4-amidinobenzyl)oxy]-1,2,3,4-tetrahydronaphthalene-2-acetic acid (Compound No. 80) hydrochloride The same reaction as described in Example 4 was carried out by using 10 ml of a methanol solution containing 0.95 g of the compound obtained in Example 24 and the entitled compound was yielded 0.9 g.

mp:251°–253° C.

$^1$HNMR(270 MHz,DMSO-d$_6$) δ ppm:9.32(brs,2H),8.97 (brs,2H), 7.82(d,2H,J=8.8 Hz),7.65(d,2H,J=8.8 Hz),6.97(d, 1H,J=8.8 Hz), 6.75(dd,1H,J=8.8,2.2 Hz),6.70(s,1H),5.22(s, 2H),2.90-2.60(m,3H), 2.40-2.22(m,3H),2.07-2.00(m,1H), 1.87-1.83(m,1H),1.45-1.30(m,1H)

EXAMPLE 26

Synthesis of ethyl 7-[(4-cyanophenoxy)methyl]-1,2,3,4-tetrahydronaphthalene-2-acetate (Compound No. 159)

(26-1) The raw material 7-methoxycarbonyl-3,4-dihydronaphthalene was prepared according to Example 5, step (5-1).

In 80 ml of tetrahydrofuran, 20 g of a 70% toluene solution of sodium bis(2-methoxyethoxy)aluminum hydride was dissolved and cooled with ice. To the solution, 20 ml of a tetrahydrofuran solution containing 10 g of 7-methoxycarbonyl-3,4-dihydronaphthalene was dropwise added and stirred for an hour at room temperature. Successively, 100 ml of a 3N aqueous hydrochloric acid solution was added with caution under ice cooling to make the solution acid, and the organic layer was extracted with ether. The ether solution was dried with anhydrous magnesium sulfate and the solvent was distilled off under reduced pressure. The concentrated residue was mixed with hexane. Formed crystals were filtered to give 7.56 g of 7-hydroxymethyl-3,4-dihydronaphthalene.

(26-2) In 150 ml of tetrahydrofuran, 7.38 g of the compound obtained in the step (26-1), 6.04 g of 4-cyanophenol and 12.0 g of diethyl azodicarboxylate were dissolved, and 13.3 g of triphenylphosphine was added by portions with ice cooling. After stirring for an hour with ice cooling, the reaction mixture was mixed with 100 ml of an 1N aqueous sodium hydroxide solution and further stirred for 30 minutes. The resulting reaction mixture was extracted with ether and dried with anhydrous magnesium sulfate. The solvent was distilled off under reduced pressure. The concentrated residue thus obtained was purified by silica gel column chromatography using a mixture, ethyl acetate:n-hexane= 1:3, as a developer to give 8.63 g of 7-[(4-cyanophenoxy) methyl]-3,4-dihydronaphthalene (26-3) The same reaction as described in Example 5, step (5-2) was carried out by using 8.2 g of the compound obtained in the step (26-2) to give 7.3 g of 7-[(4-cyanophenoxy)methyl]-1,2-epoxy-1,2,3,4-tetrahydronaphthalene.

(26-4) The same reaction as described in Example 5, step (5-3) was carried out by using 7.3 g of the compound obtained in the step (26-3) to give 4.8 g of 7-[(4-cyanophenoxy)methyl]-3,4-dihydro-(1H)-2-naphthalenone.

(26-5) The same reaction as described in Example 1, step (1-1) was carried out by using 4.74 g of the compound obtained in the step (26-4) to give 4.1 g of ethyl 7-[(4-cyanophenoxy)methyl]-3,4-dihydro-(1H)-2-naphthylidenecarboxylate.

(26-6) In a mixture composed of 50 ml of chloroform and 50 ml of ethanol, 4.0 g of the compound obtained in the step (26-5) was dissolved and subjected to a catalytic hydrogenation reaction in the presence of a Pd catalyst. The reaction mixture was filtered with Celite and the solvents were distilled off under reduced pressure to yield 3.92 g of the entitled compound.

mp:51°–52° C.

$^1$HNMR(270 MHz,CDCl$_3$) δ ppm:7.58(d,2H,J=8.8 Hz), 7.15-7.08(m,3H), 7.01(d,2H,J=8.8 Hz),5.03(s,2H),4.17(q, 2H,J=7.3 Hz),2.96-2.81(m,3H), 2.51(dd,1H,J=16.1,9.5 Hz), 2.38(d,1H,J=8.1 Hz),2.37(d,1H,J=5.9 Hz), 2.39-2.20(m,1H),1.56-1.40(m,1H),1.28(t,1H,J=7.3 Hz)

EXAMPLE 27

Synthesis of ethyl 7-[N-(4-amidinophenoxy)methyl] -1,2,3,4-tetrahydronaphthalene-2-acetate (Compound No. 83) hydrochloride The same reactions as described in Example 2 and Example 3 were carried out by using 3.5 g of the compound obtained in Example 26, step (26-6) to yield 2.15 g of the entitled compound.

mp:210°–212° C.

$^1$HNMR(270 MHz,DMSO-d$_6$) δ ppm:7.59(d,2H,J=8.8 Hz),7.34-7.22(m,3H), 7.03(d,2H,J=8.8 Hz),5.08(s,2H),4.13 (q,2H,J=7.3 Hz), 2.92-2.77(m,3H),2.58-2.48(m,1H),2.43-2.20(m,3H),1.54-1.40(m,1H), 1.21(t,3H,J=7.3 Hz)

EXAMPLE 28

Synthesis of 7-[(4-amidinophenoxy)methyl]-1,2,3,4-tetrahydronaphthalene-2-acetic acid (Compound No. 82) hydrochloride A solution composed of 1.0 g of the compound obtained in Example 27 and 20 ml of acetic acid was refluxed by heating for hours. The solvent was distilled off under reduced pressure. Crude product thus obtained was resuspended in ethanol and 10 ml of an 1M hydrochloric acid-ethanol solution was added and further stirred for an hour. The resulting solution was concentrated under reduced pressure and successively washed with water, ethanol and chloroform to yield 0.22 g of the entitled compound.

mp:above 230° C.

$^1$HNMR(270 MHz,TFA-d) δ ppm:7.63(d,2H,J=8.8 Hz), 7.39-7.27(m,3H), 7.07(d,2H,J=8.8 Hz),5.11(s,2H),3.16-3.02 (m,3H),2.72-2.62(m,1H), 2.55-2.35(m,3H),1.69-1.55(m, 1H)

EXAMPLE 29

Synthesis of ethyl 7-[(4-amidinobenzyl)amino]-1,2, 3,4-tetrahydronaphthalene-2-acetate (Compound No. 85) dihydrochloride The compound obtained in Example 1, step (1-1) was subjected to a catalytic hydrogenation reaction in the presence of a Pd catalyst to give ethyl 7-amino-1,2,3,4-tetrahydronaphth alene-2-acetate hydrochloride.

The same reaction as described in Example 23 was carried out by using 1.5 g of the compound thus obtained and 1.39 g of 4-amidinobenzyl bromide hydrochloride to yield 0.54 g of the entitled compound.

mp:175°–177° C.

$^1$HNMR(270 MHz,DMSO-d$_6$) δ ppm:9.30(brs,2H),8.96 (brs,2H), 7.78(d,2H,J=8.8 Hz),7.62(d,2H,J=8.8 Hz),6.85(d, 1H,J=8.8 Hz), 6.57(dd,1H,J=8.8,2.2 Hz),6.53(s,1H),4.43(s, 2H), 4.08(q,2H,J=7.3 Hz),2.76-2.64(m,3H),2.38-2.27(m, 3H), 2.08-1.80(m,2H),1.41-1.29(m,1H),1.15(t,3H,J=7.3 Hz)

EXAMPLE 30

Synthesis of 7-[(4-amidinobenzyl)amino]-1,2,3,4-tetrahydronaphthalene-2-acetic acid (Compound No. 84) dihydrochloride In 10 ml of 20% aqueous acetic acid solution, 0.1 g of the compound obtained in Example 29 was dissolved, 5 drops of concentrated hydrochloric acid were added, and the mixture was refluxed by heating for 2 hours. Thereafter, the solvent was distilled off under reduced pressure. The residue was dissolved in a small amount of ethanol, ether was added, and the formed precipitate was filtered and dried to yield 0.5 g of the entitled compound (amorphous).

$^1$HNMR(270 MHz,DMSO-d$_6$) δ ppm:9.22(brs,2H),8.85 (brs,2H), 7.73(d,2H,J=8.8 Hz),7.56(d,2H,J=8.8 Hz),6.73(d, 1H,J=8.8 Hz), 6.38(dd,1H,J=8.8,2.2 Hz),6.25(s,1H),4.35(s, 2H), 2.76-2.64(m,3H),2.38-2.27(m,3H),2.08-1.80(m,2H), 1.41-1.29(m,1H)

EXAMPLE 31

Synthesis of ethyl 6-[(4-cyanobenzyl)oxy]chroman-3-acetate (Compound No. 161)

(31-1) The raw material 6-methoxy-3-chromanone was prepared according to J. Med. Chem., 31, 688–691 (1988).

The same reaction as described in Example 1, step (1-1) was carried out by using 2.66 g of 6-methoxy-3-chromanone to obtain 2.7 g of ethyl 6-methoxy-3-chromanylideneacetate.

(31-2) The same reaction as described in Example 5, step (5-5) was carried out by using 2.7 g of the compound obtained in the step (31-1) to obtain 2.66 g of ethyl 6-methoxychroman-3acetate.

(31-3) In 20 ml of acetonitrile, 2.6 g of the compound obtained in the step (31-2) was dissolved, and 2.4 g of sodium iodide and 2.0 ml of chlorotrimethylsilane were added. The mixture was refluxed by heating for an hour.

The reaction mixture was thereafter poured into ice water and extracted with ethyl acetate. The organic layer was washed successively with a 10% aqueous sodium thiosulfate solution and a saturated aqueous sodium chloride solution, and dried with anhydrous magnesium sulfate. The solvent was distilled off under reduced pressure and the concentrated residue was purified by silica gel column chromatography using a mixture, ethyl acetate:n-hexane=1:3, as a developer to obtain 2.4 g of ethyl 6-hydroxychroman-3-acetate.

(31-4) The same reaction as described in Example 23 was carried out by using 2.4 g of the compound obtained in the step (31-3) to yield 3.5 g of the oily entitled compound.

$^1$HNMR(270 MHz,CDCl$_3$) δ ppm:7.67(d,2H,J=8.1 Hz), 7.52(d,2H,J=8.8 Hz), 6.76-6.72(m,2H),6.65(d,1H,J=8.8 Hz),5.04(s,2H),4.20-4.12(m,3H), 3.88-3.80(m,1H),2.95-2.88(m,1H),2.57-2.34(m,4H), 1.27(t,3H,J=7.3 Hz)

EXAMPLE 32

Synthesis of ethyl 6-[(4-amidinobenzyl)oxy] chroman-3-acetate (Compound No. 90) hydrochloride The same reactions as described in Example 2 and Example 3 were carried out by using 1.0 g of the compound obtained in Example 31, step (31-4) to yield 0.81 g of the entitled compound.

mp:157°–160° C.

$^1$HNMR(270 MHz,DMSO-d$_6$) δ ppm:8.31(s,4H),7.82(d, 2H,J=8.8 Hz), 7.62(d,2H,J=8.8 Hz),6.75-6.65(m,4H),5.12(s, 2H),4.13-4.05(m,3H), 3.77-3.70(m,1H),2.88-2.82(m,1H), 2.56-2.29(m,4H), 1.20(t,3H,J=7.3 Hz)

EXAMPLE 33

Synthesis of 6-[(4-amidinobenzyl)oxy]chroman-3-acetic acid (Compound No. 89) hydrochloride The same reaction as described in Example 4 was carried out by using 0.29 g of the compound obtained in Example 32 to yield 0.2 g of the entitled compound.

mp:222°–224° C.

$^1$HNMR(270 MHz,DMSO-d$_6$) δ ppm:9.32(brs,2H),8.97 (brs,2H), 7.82(d,2H,J=8.8 Hz),7.65(d,2H,J=8.8 Hz),6.74-6.65(m,4H),5.14(s,2H), 4.13-4.09(m,1H),3.76-3.70(m,1H), 2.86-2.81(m,1H),2.35-2.22(m,4H)

EXAMPLE 34

Synthesis of methyl 7-[(4-cyanobenzyl)oxy]-3,4-dihydronaphthalene-2-acetate (Compound No. 163)

(34-1) The raw material 7-methoxy-1-oxo-1,2,3,4-tetrahydronaphthalene-2-acetic acid was prepared according to J. Med. Chem., 32, 2277–2282 (1989).

Under cooling, 1.8 ml of thionyl chloride was dropwise added slowly to 20 ml of methanol. After 10 minutes, 1.5 g of 7-methoxy-1-oxo-1,2,3,4-tetrahydronaphthalene-2-acetic acid was added and stirred overnight at room temperature. The solvent was distilled off under reduced pressure to obtain 1.6 g of methyl 7-methoxy-1-oxo-1,2,3,4-tetrahydronaphthalene-2-acetate.

(34-2) The same reaction as described in Example 5, step (5-1) was carried out by using 1.6 g of the compound obtained in the step (34-1) to give 0.73 g of methyl 7-methoxy-3,4-dihydronaphthalene-2-acetate.

(34-3) The same reaction as described in Example 31, step (31-3) was carried out by using 0.71 g of the compound obtained in the step (34-2) to give 0.36 g of methyl a-hydroxy-3,4-dihydronaphthalene-2-acetate.

(34-4) The same reaction as described in Example 23 was carried out by using 0.36 g of the compound obtained in the step (34-3) to yield 0.5 g of the entitled compound.

mp:140°–142° C.

$^1$HNMR(270 MHz,DMSO-$d_6$) δ ppm:7.75(d,2H,J=8.8 Hz), 7.50(d,2H,J=8.8 Hz),7.02(d,1H,J=8.8 Hz),6.76-6.72 (m,2H),6.29(s,2H), 5.18(s,2H),3.62(s,3H),3.14(s,2H),2.70-2.65(m,2H),2.34-2.22(m,2H)

EXAMPLE 35

Synthesis of methyl 7-[(4-amidinobenzyl)oxy]-3,4-dihydronaphthalene-2-acetate (Compound No. 92) hydrochloride The same reactions as described in Example 2 and Example 3 were carried out by using 0.4 g of the compound obtained in Example 34, step (34-4) to yield 0.22 g of the entitled compound.

mp:192°–194° C.

$^1$HNMR(270 MHz,DMSO-$d_6$) δ ppm:8.32(s,4H),7.78(d, 2H,J=8.8 Hz), 7.59(d,2H,J=8.8 Hz),7.02(d,1H,J=8.8 Hz), 6.76-6.72(m,2H),6.29(s,2H), 5.18(s,2H),3.62(s,3H),3.14(s, 2H),2.70-2.65(m,2H),2.34-2.22(m,2H)

EXAMPLE 36

Synthesis of 7-[(4-amidinobenzyl)oxy]-3,4-dihydronaphthalene-2-acetic acid (Compound No. 91) hydrochloride The same reaction as described in Example 4 was carried out by using 0.20 g of the compound obtained in Example 35 to yield 0.1 g of the entitled compound.

mp:218°–220° C.

$^1$HNMR(270 MHz,DMSO-$d_6$) δ ppm:9.30(brs,2H),9.07 (brs,2H), 7.84(d,2H,J=8.8 Hz),7.65(d,2H,J=8.8 Hz),7.02(d, 1H,J=8.8 Hz), 6.75-6.71(m,2H),6.27(s,1H),5.21(s,2H),3.14 (s,2H),2.70-2.64(m,2H), 2.26-2.20(m,2H)

EXAMPLE 37

Synthesis of ethyl 7-[(4-guanidinobenzoyl)amino]-1,2,3,4-tetrahydronaphthalene-2-acetate (Compound No. 95) hydrochloride In 20 ml of N,N-dimethylformamide, 0.63 g of 4-guanidinobenzoic acid hydrochloride and 0.79 g of ethyl 7-amino-1,2,3,4-tetrahydronaphthalene-2-acetate hydrochloride were dissolved. To the solution, 0.036 g of 4-dimethylaminopyridine, 0.41 ml of triethylamine and 0.64 g of dicyclohexylcarbodiimide were added with cooling and stirred overnight at room temperature. The precipitate was filtered and the solvent was distilled off under reduced pressure. A saturated aqueous sodium hydrogen carbonate solution was added to the concentrated residue thus obtained and precipitated product was filtered. The precipitated product was converted to hydrochloride by treating with a hydrochloric acid-dioxane solution to yield 0.5 g of the entitled compound.

mp:100° C. (decomposed)

$^1$HNMR(270 MHz,DMSO-$d_6$) δ ppm:10.15-10.04(m,2H) ,8.05-8.02(m,2H), 7.68-7.34(m,7H),7.05-7.02(m,1H),4.11 (q,2H,J=7.34 Hz), 2.85-2.74(m,3H),2.49-2.35(m,3H),2.28-2.13(m,1H),1.91-1.78(m,1H), 1.49-1.38(m,1H),1.21(t,3H, J=7.3 Hz)

EXAMPLE 38

Synthesis of 7-[(4-guanidinobenzoyl)amino]-1,2,3,4-tetrahydronaphthalene-2-acetic acid (Compound No. 93) hydrochloride The same reaction as described in Example 30 was carried out by using 0.1 g of the compound obtained in Example 37 to yield 0.07 g of the entitled compound.

mp:140° C. (decomposed)

$^1$HNMR(270 MHz,DMSO-$d_6$) δ ppm:10.09-10.00(m,2H) ,8.05-8.02(m,2H), 7.63-7.34(m,7H),2.86-2.74(m,3H),2.39-2.24(m,3H),2.10-2.08(m,1H), 1.90-1.87(m,1H),1.45-1.33 (m,1H)

EXAMPLE 39

Synthesis of ethyl 7-[(4-aminomethylbenzoyl)amino]-1,2,3,4-tetrahydronaphthalene-2-acetate (Compound No. 124) hydrochloride (39-1) The same reaction as described in Example 37 was carried out by using a mixture composed of 0.49 g of 4-(t-butoxycarbonylaminomethyl)benzoic acid and 1.06 g of ethyl 7-amino-1,2,3,4-tetrahydronaphthalene-2-acetate hydrochroride to obtain 0.74 g of ethyl 7-[[(4-t-butoxycarbonylaminomethyl)benzoyl]amino]-1,2,3,4-tetrahydronaphthalene-2-acetate.

(39-2) In a hydrochloric acid-dioxane solution, 0.74 g of the compound obtained in the step (39-1) was dissolved and stirred for an hour at room temperature. The solvent was distilled off under reduced pressure. Ether was added to the concentrated residue and formed precipitated solid was filtered and dried to yield 0.51 g of the entitled compound.

mp:199°–201° C.

$^1$HNMR(270 MHz,DMSO-$d_6$) δ ppm:10.12(s,1H),8.39 (brs,3H), 8.00(d,2H,J=8.8 Hz),7.60(d,2H,J=8.8 Hz),7.50-7.47(m,2H), 7.03(d,1H,J=8.8 Hz),4.14-4.06(m,4H),2.86-2.75(m,3H), 2.49-2.25(m,3H),2.13-2.09(m,1H),1.91-1.87 (m,1H),1.49-1.34(m,1H), 1.21(t 3H)

EXAMPLE 40

Synthesis of 7-[(4-aminomethylbenzoyl)amino]-1,2,3,4-tetrahydronaphthalene-2-acetic acid (Compound No. 123) hydrochloride (40-1) The same reaction as described in Example 4 was carried out by using 0.74 g of the compound obtained in Example 39, step (39-1) to give 0.69 g of 7-[[4-(tert-butoxycarbonylaminomethyl)benzoyl]amino]-1,2,3,4-tetrahydronaphthalene-2-acetic acid.

(40-2) The same reaction as described in Example 39, step (39-2) was carried out by using 0.69 g of the compound obtained in the step (40-1) to yield 0.51 g of the entitled compound (amorphous). $^1$HNMR(270 MHz,DMSO-$d_6$) δ ppm:10.10(s,1H),8.33(brs,3H), 8.00(d,2H,J=8.8 Hz),7.60(d, 2H,J=8.8 Hz),7.49-7.47(m,2H), 7.03(d,1H,J=8.8 Hz),4.12 (d,2H,J=5.8 Hz),2.86-2.75(m,3H), 2.49-2.25(m,3H),2.15-2.09(m,1H),1.92-1.87(m,1H),1.49-1.34(m,1H)

PREPARATION OF A COMPARATIVE COMPOUND

Synthesis of 7-[(4-amidinobenzoyl)amino]-1-oxo-3,4-dihydroisoquinolone-2-acetic acid hydrochloride (Prep.-1) The raw material 7-nitro-1-oxo-3,4-dihydroisoquinolone was prepared according to J. Cem. Soc. Perkin I, 180 (1977) and J. Org. Chem., 48, 3220 (1983).

In 100 ml of xylene, 20 g of 7-nitro-1-oxo-3,4-dihydroisoquinolone was suspended, 0.5 g of 60% sodium hydride was added at room temperature. The mixture was refluxed under heating for an hour. Then to the mixture, 2.3 ml of ethyl bromoacetate was added and refluxed for further an hour. The reaction mixture was cooled to room temperature, and then poured to water and extracted with ethyl acetate. The extracted solution was dried with anhydrous magnesium sulfate and the solvent was distilled off under reduced pressure. The obtained crude product was purified by silica gel column chromatography using a mixture, chloroform: methanol=40:1, as a developer to give 0.67 g of ethyl 7-nitro-1-oxo-3,4-dihydroisoquinolone-2-acetate.

(Prep.-2) In 10 ml of ethanol, 0.67 g of the compound obtained in step (Prep.-1) was solved. To the mixture, 1N hydrochloride/ethanol solution was added and the mixture was subjected to a catalytic hydrogenation reaction in the presence of a Pd catalyst. Formed precipitate was filtrated and washed with ether to give 0.65 g of ethyl 7-amino-1-oxo-3,4-dihydroisoquinolone-2-acetate hydrochloride.

(Prep.-3) The same reaction as described in Example 1, step (1-2) was carried out by using 0.62 g of the compound thus obtained by step (Prep.-2) and 0.49 g of 4-cyanobenzoyl chloride to give 0.85 g of ethyl 7-[(4-cyanobenzoyl)amino]-1-oxo-3,4-dihydroisoquinolone-2-acetate.

(Prep.-4) The same reaction as described in Example 2 and Example 3 was carried out by using 0.55 g of the compound thus obtained by step (Prep.-3) to give 0.56 g of ethyl 7-[(4-amidinobenzoyl)amino]-1-oxo-3,4-dihydroisoquinolone-2-acetate hydrochloride.

(Prep.-5) The same reaction as described in Example 4 was carried out by using 0.52 g of the compound thus obtained by step (Prep.-4) to yield 0.28 g of the entitled compound.

mp:295°–297° C. (Decomposed)

$^1$HNMR(270 MHz,TFA-d) δ ppm:8.25(m,3H),8.03(m, 3H), 7.49(d,1H,J=8.8 Hz),4.68(s,2H),3.94(t,2H,J=7.3 Hz), 3.27(t,2H,J=7.3 Hz)

PHARMACOLOGICAL TEST EXAMPLE

1. Inhibition of platelet aggregation in Guinea pig

Blood of male guinea pig was collected with an injection syringe which contains 3.8% sodium citrate as an anticoagulant in a ratio of 1 volume to 9 volumes of the blood. Successively, the collected blood mixture was subjected to centrifugation at 120×g for 15 minutes at room temperature to obtain platelet-rich plasma (PRP). The residual blood after separating PRP was further subjected to centrifugation at 1,200×g for 15 minutes to obtain platelet-poor plasma (PPP). Numbers of the platelet in PRP were measured with an automatic platelet counter: Sysmex PL-100 (manufactured by Toa Iyodensi Co.) and PRP was diluted with PPP so as to adjust a platelet concentration to be about 300,000 particles/μl. Platelet aggregation was measured by the following procedure with a 6 channel aggregometer: HEMA TRACER 1 (manufactured by NKK Co.).

After warming 240 μl of PRP at 37° C. for 2 minutes, 30 μl of the solvent of specimen as a control or of the specimen having various concentrations was added to PRP. Further 2 minutes later, 30 μl of adenosine diphosphate (final concentration: 5 μM) was added to induce platelet aggregation. An inhibition percentage was obtained by comparing the maximum aggregation rate of the specimen drug group with that of control. A specimen drug concentration at 50% inhibition ($IC_{50}$) was calculated from the inhibition percentage and the specimen drug concentration, and used as an index of antiplatelet activity. Results are illustrated in Table 1.

2. Inhibition of platelet aggregation in human

Blood was collected from healthy human volunteers with an injection syringe and mixed one volume of 3.8% sodium citrate as an anticoagulant to 9 volumes of the blood. Successively, the obtained blood mixture was subjected to centrifugation at 120×g for 15 minutes at room temperature to obtain platelet-rich plasma (PRP). The residual blood after separating the PRP was further subjected to centrifugation at 1,200×g for 20 minutes to obtain platelet-poor plasma (PPP). Numbers of the platelet were measured with an automatic platelet counter: Sysmex PL-100 (manufactured by Toa Iyodensi Co.) and PRP was diluted with PPP so as to adjust a platelet concentration to be about 250,000 particles/μl. Platelet aggregation was measured by the following procedure with a 6 channel aggregometer: HEMA TRACER 1 (manufactured by NKK Co.)

After warming 240 μl of PRP at 37° C. for 2 minutes, 30 μl of the solvent of specimen as a control or the specimen having various concentrations was added to PRP. Further 2 minutes later, 30 μl of adenosine diphosphate (final concentration: 5 μM) was added to induce platelet aggregation. An inhibition percentage was obtained by comparing the maximum aggregation rate of the specimen drug group with that of control. A specimen drug concentration at 50% inhibition ($IC_{50}$) was calculated from the inhibition percentage and the specimen drug concentration, and used as an index of anti platelet activity. Results are illustrated in Table 2.

TABLE 1

| Inhibition of platelet aggregation in Guinea pig | |
| --- | --- |
| compound No. | $IC_{50}$ (μM) |
| 1 | 0.37 |
| 3 | 0.4 |
| 9 | 0.23 |
| 11 | 0.34 |
| 17 | 0.48 |
| 28 | 6.6 |
| 37 | 4.3 |
| 47 | 1.77 |
| 56 | 0.34 |
| 80 | 18 |
| 81 | 22 |
| 82 | 39 |
| 84 | 24 |
| 89 | 12 |
| 90 | 17 |
| 91 | 41 |
| 93 | 27 |
| 123 | 14 |
| Comparative compound | >100 |

TABLE 2

| Inhibition of platelet aggregation in Human | |
|---|---|
| compound No. | IC$_{50}$ (μM) |
| 1 | 0.057 |
| 9 | 0.046 |
| 17 | 0.049 |
| 28 | 0.293 |
| 47 | 0.194 |
| 56 | 0.115 |
| 80 | 1.5 |
| Comparative compound | 3.9 |

As shown in the above test results, the compounds represented by the formula (1) in the invention have more excellent antiplatelet activity than the Comparative compound which is described in WO 94/29273. A particularly excellent antiplatelet activity is exerted in the compound represented by the formula (1) in the invention wherein B is -CON(R$^1$)- or -N(R$^1$)CO-, W-X is

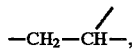

and Y is -CH$_2$- or -O-, wherein R$^1$ is a hydrogen atom or an alkyl group having 1 to 4 carbon atoms.

PHARMACEUTICAL FORMULATION EXAMPLE

When the compound represented by the formula (1) in the invention is used for a remedy of thrombosis, the compound can be used, for example, by the following formulations.

Formulation Example 1 (Tablet)

After thoroughly mixing 50 g of 7-[(4-amidinobenzoyl)amino]-1,2,3,4-tetrahydronaphthalene-2-acetic acid (Compound No. 1), 38 g of lactose, 35 g of corn starch and 20 g of crystalline cellulose, the mixture was subjected to scouring granulation with an aqueous solution containing 5 g of hydroxypropyl cellulose and dried at 50° C. for 4 hours. To the granule obtained, 2 g of magnesium stearate was added and thoroughly mixed. The mixture thus obtained was subjected to tablet making with a tabletting machine to form tablets having a weight of 150 mg/tablet.

Formulation Example 2 (Capsule)

After throughly mixing 100 g of 7-[N-(4-amidinophenyl)carbamoyl]-1,2,3,4-tetrahydronaphthalene-2-acetic acid (Compound No. 9), 70 g of lactose, 70 g of corn starch, 40 g of crystalline cellulose and 6 g of magnesium stearate, the mixture obtained was packed into a hard gelatin capsule with a plugger to form capsules having a content of 300 mg.

Formulation Example 3 (Granule)

After throughly mixing 100 g of 6-[N-(4-amidinobenzoyl)amino]chroman-3-acetic acid (Compound No. 17), 150 g of lactose, 140 g of corn starch and 80 g of crystalline cellulose, the mixture was subjected to scouring granulation with a solution containing 20 g of hydroxypropyl cellulose in 400 ml of water and dried at 50° C. for 4 hours. The granulated mass was graded by passing through a 12 mesh screen and thoroughly mixed with 8 thoroughly mixed with 8 g of magnesium stearate to obtain granules.

Formulation Example 4 (Injection)

An ampoule was mounted with 0.5 g of 7-[N-(4-amidinophenyl)carbamoyl]-1,2,3,4-tetrahydronaphthalene-2-acetic acid (Compound No. 9) and 5.0 ml of cotton seed oil to make a nonaqueous injection. In the case of an injection for infusion, 1.0 g of polyoxyethylene hardened castor oil 60 (HCO-60) as a surfactant was added to the above obtained solution. The mixture was suspended in 200 ml of 0.9% physiological saline at the time of use.

What is claimed is:

1. A compound or a pharmaceutically acceptable salt thereof represented by the formula (1):

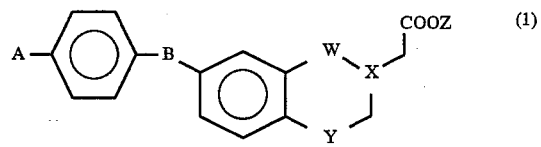

wherein A is an amidino group, guanidino group or aminomethyl group, B is -CH$_2$O-, -OCH$_2$-, -CH$_2$N(R$^1$)-, -N(R$^1$)CH$_2$-, -CON(R$^1$)- or -N(R$^1$) CO-, wherein R$^1$ is a hydrogen atom or an alkyl group having 1–4 carbon atoms: W-X [-CH$_2$-CH=, -CH$_2$-N= or -CH=C=]

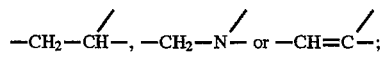

Y is -CH$_2$- or -O-, with the proviso that when W-X is

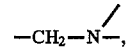

Y is not -O-; and Z is a hydrogen atom or an alkyl group having 1–4 carbon atoms.

2. The compound or the pharmaceutically acceptable salt thereof according to claim 1 wherein A is an amidino group.

3. The compound or the pharmaceutically acceptable salt thereof according to claim 2, wherein B is -CON(R$^1$)- or -N(R$^1$)CO-, R$^1$ is a hydrogen atom or an alkyl group having 1–4 carbon atoms, and W-X is [-CH$_2$-CH= or -CH$_2$-N=]-

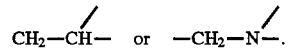

4. The compound or the pharmaceutically acceptable salt thereof according to claim 3 wherein R$^1$ is a hydrogen atom.

5. 7-[(4-amidinobenzoyl)amino]-1,2,3,4-tetrahydronaphthalene-2-acetic acid, 7-[N-(4-amidinophenyl)carbamoyl]-1,2,3,4-tetrahydronaphthalene-2-acetic acid, 6-[(4-amidinobenzoyl) amino]chroman-3-acetic acid, 7-[(4-amidinobenzoyl)amino]-1,2,3,4-tetrahydroisoquinoline-2-acetic acid or a pharmaceutically acceptable salt thereof.

6. A compound or a pharmaceutically acceptable salt thereof represented by the formula (2):

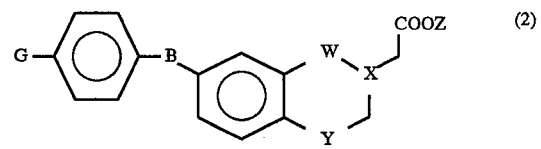

wherein G is a cyano group or HN=C(OR$^2$)-, wherein R$^2$ is an alkyl group having 1–4 carbon atoms; B is -CH$_2$O-, -OCH$_2$-, -CH$_2$N(R$^1$)-, -N(R$^1$)CH$_2$-, -CON(R$^1$)- or -N(R$^1$)

CO-, wherein $R^1$ is a hydrogen atom or an alkyl group having 1–4 carbon atoms; W-X is [-CH$_2$-CH=, -CH$_2$-N= or -CH=C]

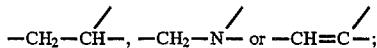

Y is -CH$_2$- or -O-, with the proviso that when W-X is

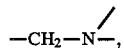

Y is not -O-; and Z is a hydrogen atom or an alkyl group having 1–4 carbon atoms.

7. The compound or the pharmaceutically acceptable salt thereof according to claim 6, wherein B is -CONH- or -NHCO-, W-X is [-CH$_2$-CH= or -CH$_2$-N=]

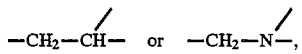

and Y is -CH$_2$- or -O-.

8. A pharmaceutical composition of matter comprising a compound according to claim 1 in an amount effective for inhibiting platelet aggregation and a pharmaceutically acceptable diluent and/or carrier therefor.

9. A pharmaceutical composition of matter comprising a compound according to claim 2 in an amount effective for inhibiting platelet aggregation and a pharmaceutically acceptable diluent and/or carrier therefor.

10. A pharmaceutical composition of matter comprising a compound according to claim 3 in an amount effective for inhibiting platelet aggregation and a pharmaceutically acceptable diluent and/or carrier therefor.

11. A pharmaceutical composition of matter comprising a compound according to claim 4 in an amount effective for inhibiting platelet aggregation and a pharmaceutically acceptable diluent and/or carrier therefor.

12. A pharmaceutical composition of matter comprising a compound according to claim 5 in an amount effective for inhibiting platelet aggregation and a pharmaceutically acceptable diluent and/or carrier therefor.

13. A method for preventing or remedying thrombosis comprising administering to a patient in need of such treatment a compound according to claim 1 in an amount effective for preventing or remedying thrombosis.

14. A method for preventing or remedying restenosis after percutaneous transluminal coronary angioplasty or percutaneous transluminal coronary recanalization comprising administering to a patient in need of such treatment a compound according to claim 1 in an amount effective for preventing or remedying restenosis after percutaneous transluminal coronary angioplasty or percutaneous transluminal coronary recanalization.

15. A method for preventing or remedying reocclusion after percutaneous transluminal coronary angioplasty or percutaneous transluminal coronary recanalization comprising administering to a patient in need of such treatment a compound according to claim 1 in an amount effective for preventing or remedying reocclusion after percutaneous transluminal coronary angioplasty or percutaneous transluminal coronary recanalization.

16. A method for preventing or remedying thrombosis comprising administering to a patient in need of such treatment a compound according to claim 2 in an amount effective for preventing or remedying thrombosis.

17. A method for preventing or remedying restenosis after percutaneous transluminal coronary angioplasty or percutaneous transluminal coronary recanalization comprising administering to a patient in need of such treatment a compound according to claim 2 in an amount effective for preventing or remedying restenosis after percutaneous transluminal coronary angioplasty or percutaneous transluminal coronary recanalization.

18. A method for preventing or remedying reocclusion after percutaneous transluminal coronary angioplasty or percutaneous transluminal coronary recanalization comprising administering to a patient in need of such treatment a compound according to claim 2 in an amount effective for preventing or remedying reocclusion after percutaneous transluminal coronary angioplasty or percutaneous transluminal coronary recanalization.

19. A method for preventing or remedying thrombosis comprising administering to a patient in need of such treatment a compound according to claim 3 in an amount effective for preventing or remedying thrombosis.

20. A method for preventing or remedying restenosis after percutaneous transluminal coronary angioplasty or percutaneous transluminal coronary recanalization comprising administering to a patient in need of such treatment a compound according to claim 3 in an amount effective for preventing or remedying restenosis after percutaneous transluminal coronary angioplasty or percutaneous transluminal coronary recanalization.

21. A method for preventing or remedying reocclusion after percutaneous transluminal coronary angioplasty or percutaneous transluminal coronary recanalization comprising administering to a patient in need of such treatment a compound according to claim 3 in an amount effective for preventing or remedying reocclusion after percutaneous transluminal coronary angioplasty or percutaneous transluminal coronary recanalization.

22. A method for preventing or remedying thrombosis comprising administering to a patient in need of such treatment a compound according to claim 4 in an amount effective for preventing or remedying thrombosis.

23. A method for preventing or remedying restenosis after percutaneous transluminal coronary angioplasty or percutaneous transluminal coronary recanalization comprising administering to a patient in need of such treatment a compound according to claim 4 in an amount effective for preventing or remedying restenosis after percutaneous transluminal coronary angioplasty or percutaneous transluminal coronary recanalization.

24. A method for preventing or remedying reocclusion after percutaneous transluminal coronary angioplasty or percutaneous transluminal coronary recanalization comprising administering to a patient in need of such treatment a compound according to claim 4 in an amount effective for preventing or remedying reocclusion after percutaneous transluminal coronary angioplasty or percutaneous transluminal coronary recanalization.

25. A method for preventing or remedying thrombosis comprising administering to a patient in need of such treatment a compound according to claim 5 in an amount effective for preventing or remedying thrombosis.

26. A method for preventing or remedying restenosis after percutaneous transluminal coronary angioplasty or percutaneous transluminal coronary recanalization comprising administering to a patient in need of such treatment a compound according to claim 5 in an amount effective for preventing or remedying restenosis after percutaneous transluminal coronary angioplasty or percutaneous transluminal coronary recanalization.

27. A method for preventing or remedying reocclusion after percutaneous transluminal coronary angioplasty or percutaneous transluminal coronary recanalization comprising administering to a patient in need of such treatment a compound according to claim 5 in an amount effective for preventing or remedying reocclusion after percutaneous transluminal coronary angioplasty or percutaneous transluminal coronary recanalization.

* * * * *